US010942636B2

(12) United States Patent
Okabe et al.

(10) Patent No.: US 10,942,636 B2
(45) Date of Patent: Mar. 9, 2021

(54) DISPLAY CONTROL DEVICE, METHOD FOR OPERATING DISPLAY CONTROL DEVICE, AND PROGRAM FOR OPERATING DISPLAY CONTROL DEVICE

(71) Applicant: FUJIFILM Corporation, Tokyo (JP)

(72) Inventors: Yuki Okabe, Tokyo (JP); Eiichi Imamichi, Tokyo (JP); Yuya Kudo, Tokyo (JP); Masaki Miyamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/845,021

(22) Filed: Apr. 9, 2020

(65) Prior Publication Data
US 2020/0326835 A1    Oct. 15, 2020

(30) Foreign Application Priority Data

Apr. 11, 2019    (JP) .............................. JP2019-075796

(51) Int. Cl.
*G06F 3/0486*    (2013.01)
*G06F 3/0484*    (2013.01)
(Continued)

(52) U.S. Cl.
CPC ........ *G06F 3/04845* (2013.01); *G06F 3/0482* (2013.01); *G06F 3/0486* (2013.01);
(Continued)

(58) Field of Classification Search
CPC .. G06F 3/04845; G06F 3/0482; G06F 3/0486; G09G 5/14; G09G 2380/08; G09G 2354/00; G16H 30/40
See application file for complete search history.

(56) References Cited

U.S. PATENT DOCUMENTS 7,058,901 B1 * 6/2006 Hafey .................... G16H 40/63
715/792
7,170,532 B2 * 1/2007 Sako .................... G06T 7/0012
345/637
(Continued)

FOREIGN PATENT DOCUMENTS

JP    2002143095    5/2002

*Primary Examiner* — Yongjia Pan
(74) *Attorney, Agent, or Firm* — JCIPRNET

(57) ABSTRACT

A display control device includes: a first display control unit that displays, on a display screen, a display region in which a plurality of display frames are arranged and a selection region in which a list of a plurality of thumbnail images obtained by reducing each of a plurality of examination images is displayed; a receiving unit that receives an operation of selecting the plurality of thumbnail images from the selection region to select the plurality of examination images corresponding to the plurality of thumbnail images; a comparison unit that recognizes the number of selected examination images and compares the recognized number of selected examination images with the current number of display frames; a change unit that changes the number of display frames in the display region and adds the display frame in the display region in a case in which the number of display frames is less than the number of selected examination images; and a second display control unit that lays out and displays the plurality of selected examination images in the plurality of display frames.

11 Claims, 16 Drawing Sheets

(51) Int. Cl.
*G16H 30/40* (2018.01)
*G09G 5/14* (2006.01)
*G06F 3/0482* (2013.01)

(52) U.S. Cl.
CPC ............... *G09G 5/14* (2013.01); *G16H 30/40* (2018.01); *G09G 2354/00* (2013.01); *G09G 2380/08* (2013.01)

(56) References Cited

U.S. PATENT DOCUMENTS

| | | | | |
|---|---|---|---|---|
| 7,859,549 | B2* | 12/2010 | Handley | H04N 1/0045 |
| | | | | 345/619 |
| 8,225,199 | B2* | 7/2012 | Okubo | G06F 16/58 |
| | | | | 715/243 |
| 9,262,444 | B2* | 2/2016 | Gross | G06F 3/04842 |
| 9,398,887 | B2* | 7/2016 | Miyazawa | G06F 19/321 |
| 2002/0080918 | A1* | 6/2002 | Sako | A61B 6/548 |
| | | | | 378/115 |
| 2005/0143641 | A1* | 6/2005 | Tashiro | G06T 19/00 |
| | | | | 600/407 |
| 2005/0259116 | A1* | 11/2005 | Araoka | G16H 40/63 |
| | | | | 345/619 |
| 2007/0050726 | A1* | 3/2007 | Wakai | G06F 3/0486 |
| | | | | 715/769 |
| 2009/0054755 | A1* | 2/2009 | Shiibashi | G06Q 50/24 |
| | | | | 600/407 |
| 2009/0132588 | A1* | 5/2009 | Mahesh | G06Q 10/00 |
| 2009/0213034 | A1* | 8/2009 | Wu | G16H 30/20 |
| | | | | 345/1.1 |
| 2010/0131890 | A1* | 5/2010 | Natanzon | G06F 3/04845 |
| | | | | 715/808 |
| 2013/0088512 | A1* | 4/2013 | Suzuki | A61B 6/463 |
| | | | | 345/629 |
| 2015/0082220 | A1* | 3/2015 | Lane | A61N 5/1039 |
| | | | | 715/771 |
| 2015/0317434 | A1* | 11/2015 | Kondo | A61B 5/00 |
| | | | | 705/3 |
| 2018/0292963 | A1* | 10/2018 | Nanjo | G06T 7/0012 |

* cited by examiner

DISPLAY CONTROL DEVICE, METHOD FOR OPERATING DISPLAY CONTROL DEVICE, AND PROGRAM FOR OPERATING DISPLAY CONTROL DEVICE

CROSS-REFERENCE TO RELATED APPLICATION

This application claims priority from Japanese Patent Application No. 2019-075796, filed on Apr. 11, 2019, the disclosure of which is incorporated by reference herein in its entirety.

BACKGROUND

Field of the Invention

The present disclosure relates to a display control device, a method for operating a display control device, and a program for operating a display control device.

Related Art

In recent years, in the field of medical image diagnosis, in addition to X-ray imaging apparatuses, imaging apparatuses (hereinafter, referred to as modalities) using various techniques, such as computed tomography (CT) apparatuses, ultrasound (US) diagnostic apparatuses, magnetic resonance imaging (MRI) apparatuses, positron emission tomography (PET) apparatuses, and single-photon emission computed tomography (SPECT) apparatuses, have been used. In the modalities, a plurality of examination images are acquired in one examination. Then, a plurality of series, each of which includes a plurality of examination images acquired for each examination, are acquired by different modalities under different imaging conditions.

In contrast, in the related art, comparative interpretation has been performed which displays a plurality of examination images on a display device, such as a liquid crystal display, and interprets the examination images while comparing the examination images. For example, for the examination image of a patient that is an example of a subject, the examination images of the same patient in the current examination and the past examination are displayed and comparative interpretation is performed to check the degree of progress of a lesion or to find abnormality at an early stage. In addition, in many cases, useful diagnostic results are obtained by performing comparative interpretation for a plurality of examination images acquired in a plurality of examinations of different types such as a CT examination and an ultrasound examination.

Further, in order to perform a diversified image diagnosis, it is desired to perform comparative interpretation between different types of examination images acquired, for example, under different imaging conditions and by different modalities and comparative interpretation between the current examination image and the past examination image acquired by the same type of examinations. In a case in which comparative interpretation is performed between a plurality of examination images, it is necessary to select a plurality of examination images to be subjected to comparative interpretation, to lay out the plurality of selected examination images such that they can be compared with each other, and to display the plurality of selected examination images on a display unit.

Therefore, various techniques have been proposed in order to lay out a plurality of examination images to be subjected to comparative interpretation in a display region for observation in a display screen such that comparative interpretation can be performed for the plurality of examination images. For example, in a display control device described in JP2002-143095A, in a case in which the doctor's opinion is input, display conditions, such as the number of divisions and image arrangement in a display region, which have been stored in advance in association with the input opinion are set and examination images are displayed on a display screen according to the set display conditions.

However, in the technique described in JP2002-143095A, the display conditions, such as the number of divisions and image arrangement in the display region, associated with the opinion input by the doctor are set. Therefore, for example, in a case in which the number of examination images for which the doctor actually wants to perform comparative interpretation is less than the preset number of divisions of the display region, the doctor needs to reset the display conditions according to the lack of the number of examination images for which the doctor wants to perform comparative interpretation, and operability is reduced.

SUMMARY

The present disclosure has been made in view of the above-mentioned problems and an object of the present disclosure is to provide a display control device, a method for operating a display control device, and a program for operating a display control device that can improve user operability.

According to the present disclosure, there is provided a display control device comprising: a first display control unit that performs first display control to display, on a display screen, a display region in which a plurality of examination images acquired for each examination are displayed and which has a plurality of display frames capable of being laid out as display positions of the plurality of examination images and a selection region which is used to select the plurality of examination images laid out in the plurality of display frames and in which a list of a plurality of thumbnail images obtained by reducing each of the plurality of examination images is displayed; a receiving unit that receives an operation of selecting the plurality of thumbnail images from the selection region to select the plurality of examination images corresponding to the plurality of thumbnail images; a comparison unit that recognizes the number of examination images selected by the selection operation and compares the recognized number of selected examination images with the current number of display frames; a change unit that changes the number of display frames in the display region and adds the display frame in the display region in a case in which the number of display frames is less than the number of selected examination images; and a second display control unit that performs second display control to lay out and display the plurality of selected examination images in the plurality of display frames.

In the display control device according to the present disclosure, the change unit may delete the display frame in the display region in a case in which the number of display frames is greater than the number of selected examination images.

In the display control device according to the present disclosure, a command to lay out the examination images in the display frames may be an operation of dragging the plurality of thumbnail images selected in the selection region from the selection region to the display region or a miniature window obtained by reducing grid-shaped arrangement of the plurality of display frames and dropping the plurality of thumbnail images to the display region or the miniature window.

Further, in the display control device according to the present disclosure, the designation operation is not limited to the drag and drop operation and may be an operation of selecting a thumbnail image and then clicking a designated position with, for example, a pointer indicating a position.

In the display control device according to the present disclosure, the second display control unit may display the same number of miniature display frames as the number of selected examination images in the miniature window in a state in which the plurality of thumbnail images are selected in the selection region and before the same number of display frames as the number of selected examination images is laid out in the display region.

In the display control device according to the present disclosure, on the display screen, the miniature window may not be displayed before the plurality of thumbnail images are selected and may be displayed in a case in which the drag of the plurality of selected thumbnail images is started after the plurality of thumbnail images are selected in the selection region.

In the present disclosure, "the case in which the drag is started" may be the timing when the drag operation is started or immediately before the drag operation is started, specifically, the timing when a left button of a mouse is pressed on a region of any one of the plurality of thumbnail images.

In the display control device according to the present disclosure, the second display control unit may display the miniature window at a position where a drag distance of the thumbnail image from the selection region to the miniature window is shorter than a drag distance of the thumbnail image from the selection region to the display region.

In the display control device according to the present disclosure, the receiving unit may further receive a selection order in which the plurality of thumbnail images are selected and the second display control unit may lay out the plurality of examination images in the plurality of display frames in the selection order.

In the display control device according to the present disclosure, the first display control unit may use the number and arrangement of the display frames preset for each user as initial display settings for each user at startup.

In the display control device according to the present disclosure, the examination images displayed in the display frames in the display region may include a representative image of a plurality of examination images acquired in the same examination. In a case in which the examination image displayed in the display frame is the representative image, the plurality of examination images may be selectively displayed in the display frame.

In the display control device according to the present disclosure, in a case in which the plurality of selected examination images include a current examination image and a past examination image that are the same type and have been acquired in examinations which are the same type and were made on different examination dates, the second display control unit may lay out the current examination image and the past examination image at positions adjacent to each other in a column direction or a row direction.

According to the present disclosure, there is provided a method for operating a display control device. The method comprises: a first display control step of performing first display control to display, on a display screen, a display region in which a plurality of examination images acquired for each examination are displayed and which has a plurality of display frames capable of being laid out as display positions of the plurality of examination images and a selection region which is used to select the plurality of examination images laid out in the plurality of display frames and in which a list of a plurality of thumbnail images obtained by reducing each of the plurality of examination images is displayed; a receiving step of receiving an operation of selecting the plurality of thumbnail images from the selection region to select the plurality of examination images corresponding to the plurality of thumbnail images; a comparison step of recognizing the number of examination images selected by the selection operation and comparing the recognized number of selected examination images with the current number of display frames; a change step of changing the number of display frames in the display region and adding the display frame in the display region in a case in which the number of display frames is less than the number of selected examination images; and a second display control step of performing second display control to lay out and display the plurality of selected examination images in the plurality of display frames.

According to the present disclosure, there is provided a program for operating a display control device. The program causes a computer to function as: a first display control unit that perforans first display control to display, on a display screen, a display region in which a plurality of examination images acquired for each examination are displayed and which has a plurality of display frames capable of being laid out as display positions of the plurality of examination images and a selection region which is used to select the plurality of examination images laid out in the plurality of display frames and in which a list of a plurality of thumbnail images obtained by reducing each of the plurality of examination images is displayed; a receiving unit that receives an operation of selecting the plurality of thumbnail images from the selection region to select the plurality of examination images corresponding to the plurality of thumbnail images; a comparison unit that recognizes the number of examination images selected by the selection operation and compares the recognized number of selected examination images with the current number of display frames; a change unit that changes the number of display frames in the display region and adds the display frame in the display region in a case in which the number of display frames is less than the number of selected examination images; and a second display control unit that performs second display control to lay out and display the plurality of selected examination images in the plurality of display frames.

According to the present disclosure, there is provided another display control device comprising a memory that stores commands to be executed by a computer and a processor that is configured to execute the stored commands. The processor performs: a first display control step of performing first display control to display, on a display screen, a display region in which a plurality of examination images acquired for each examination are displayed and which has a plurality of display frames capable of being laid out as display positions of the plurality of examination images and a selection region which is used to select the plurality of examination images laid out in the plurality of display frames and in which a list of a plurality of thumbnail images obtained by reducing each of the plurality of examination images is displayed; a receiving step of receiving an operation of selecting the plurality of thumbnail images from the selection region to select the plurality of examination images corresponding to the plurality of thumbnail images; a comparison step of recognizing the number of examination images selected by the selection operation and comparing the recognized number of selected examination images with the current number of display frames; a change step of changing the number of display frames in the display region and adding the display frame in the display region in a case in which the number of display frames is less than the number of selected examination images; and a second display control step of performing second display control to lay out and display the plurality of selected examination images in the plurality of display frames.

According to the display control device, the method for operating the display control device, and the program for operating the display control device of the present disclosure, it is possible to improve user operability.

DETAILED DESCRIPTION

Figure 1:
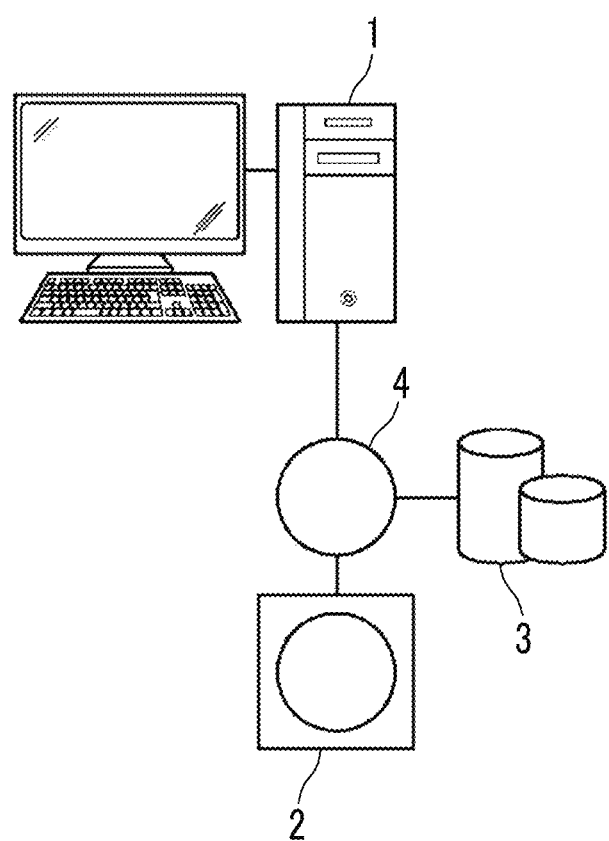
FIG. 1 is a hardware configuration diagram illustrating the outline of a diagnosis support system to which a display control device according to an embodiment of the present disclosure is applied.

Hereinafter, a first embodiment of the present disclosure will be described with reference to the drawings. FIG. 1 is a hardware configuration diagram illustrating the outline of a diagnosis support system to which a display control device according to an embodiment of the present disclosure is applied. As illustrated in FIG. 1, in the diagnosis support system, a display control device 1, a three-dimensional imaging apparatus 2, and an image storage server 3 according to this embodiment are connected to each other through a network 4 so as to be communicable.

The three-dimensional imaging apparatus 2 is an apparatus that captures an image of a diagnosis target part of a patient that is an example of a subject and generates a three-dimensional image indicating the part. Specifically, examples of the three-dimensional imaging apparatus 2 include a CT apparatus, an MRI apparatus, a PET apparatus, and a SPECT apparatus. An examination image generated by the three-dimensional imaging apparatus 2 is transmitted to the image storage server 3 and is then stored therein.

The image storage server 3 is a computer that stores and manages various kinds of data and comprises a large-capacity external storage device and database management software. The image storage server 3 communicates with other apparatuses through the wired or wireless network 4 to transmit and receive, for example, image data. Specifically, the image storage server 3 acquires various kinds of data including image data of the three-dimensional image generated by the three-dimensional imaging apparatus 2 through the network, stores the data in a recording medium, such as a large-capacity external storage device, and manages the stored data. The storage format of the image data and the communication between the apparatuses through the network 4 are based on a protocol such as Digital Imaging and Communication in Medicine (DICOM).

In this embodiment, the image storage server 3 stores various kinds of data including image data of a plurality of patients. For example, the image storage server 3 stores, as data stored for each patient, the three-dimensional image and accessory information of the patient acquired for each of the examinations performed for the same patient at different times and the three-dimensional image and accessory information of the patient acquired for each of the examinations performed for the same patient under different imaging conditions. For example, the image storage server 3 stores a plurality of series each of which includes a plurality of examination images acquired in one examination, such as abdominal CT or head MRI, for the current examination and the past examination. In the present disclosure, the three-dimensional image is a set of a plurality of slice images (tomographic images) output by a tomographic apparatus, such as a CT apparatus or an MRI apparatus, and is also referred to as volume data. Further, in the present disclosure, volume data acquired by one imaging operation is referred to as "series". In this embodiment, each of the plurality of slice images included in the series is an example of an examination image. Among the examination images, the examination images included in the same series are particularly referred to as same-seriesexamination images.

The accessory information includes, for example, the following information: an image identification (ID) for identifying each image, a patient ID for identifying a subject, an examination ID for identifying an examination, a unique identification (UID) that is assigned to each examination image, an examination date and time when the examination image was generated, the type of modality used in the examination for acquiring the examination image, patient information including the name, age, and sex of a patient, an examination part (imaging part), imaging conditions (whether or not a contrast agent is used or a radiation dose), and a series number in a case in which a plurality of examination images are acquired by one examination.

Figure 2:
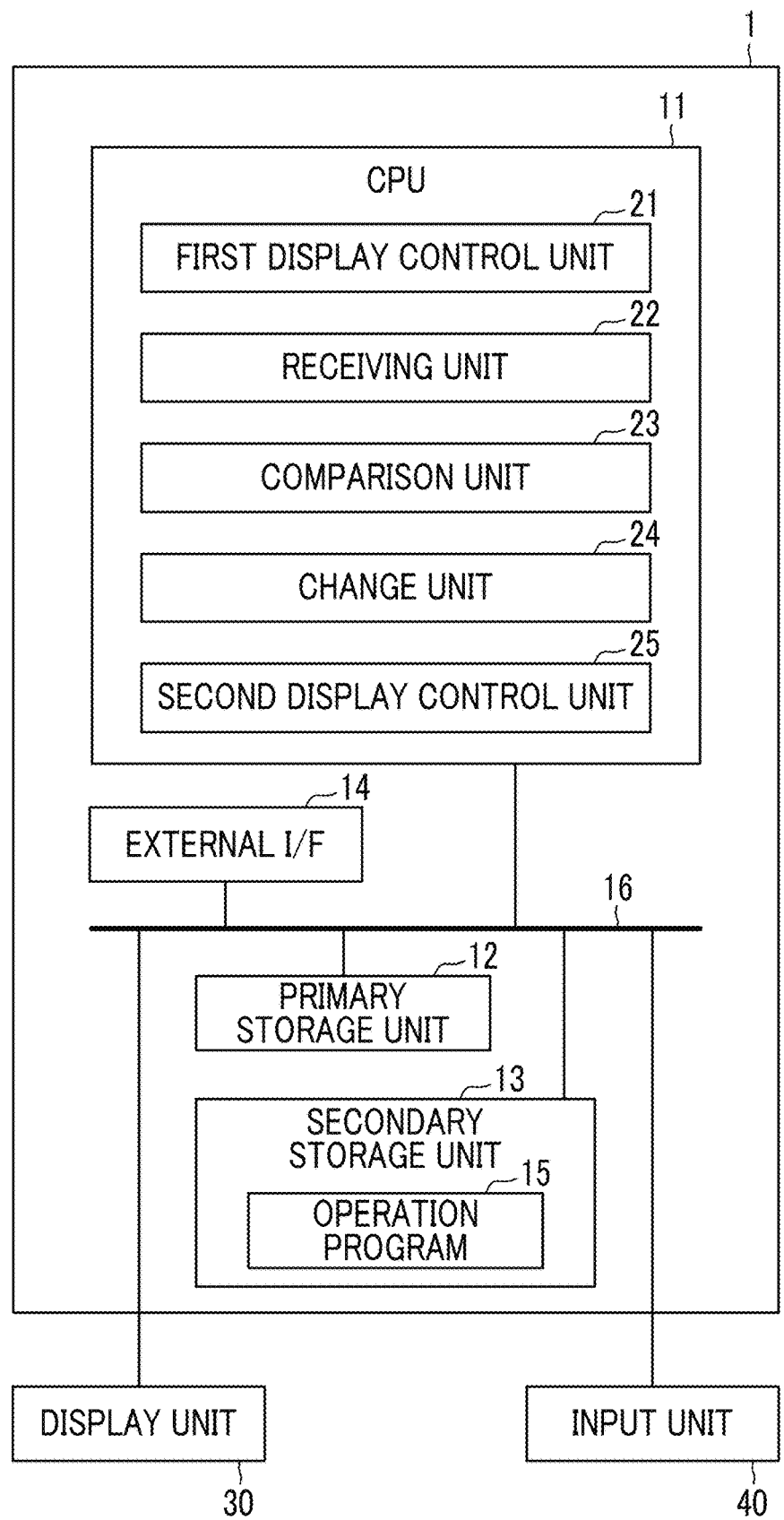
FIG. 2 is a block diagram schematically illustrating the configuration of a display control device according to a first embodiment of the present disclosure.

Next, the configuration of the display control device 1 will be described. FIG. 2 is a block diagram illustrating the configuration of a display control device 1 according to a first embodiment.

The display control device 1 is a computer comprising, for example, a central processing unit (CPU) 11, a primary memory 12, a secondary memory (storage unit) 13, an external interface (I/F) 14. The CPU 11 controls the entire display control device 1. The primary memory 12 is a volatile memory that is used as a work area in a case in which various programs are executed. An example of the primary memory 12 is a random access memory (RAM). The secondary memory 13 is a non-volatile memory in which various programs and various parameters are stored in advance. An embodiment of an operation program 15 of the display control device 1 according to the invention is installed in the secondary memory 13.

The operation program 15 is recorded on a recording medium, such as a digital versatile disc (DVD) or a compact disc read only memory (CD-ROM), is distributed, and is then installed in a computer from the recording medium. Alternatively, the operation program 15 may be stored in a storage device of a server computer connected to the network or a network storage such that it can be accessed from the outside, may be downloaded to the computer in response to a request from the outside, and may be installed.

The CPU 11 executes the operation program 15 to function as a first display control unit 21, a receiving unit 22, a comparison unit 23, a change unit 24, and a second display control unit 25. An example of the secondary memory 13 is an electrically erasable programmable read-only memory (EEPROM) or a flash memory.

The external I/F 14 transmits and receives various kinds of information between the display control device 1 and the image storage server 3. The CPU 11, the primary memory 12, the secondary memory 13, and the external I/F 14 are connected to a bus line 16 which is a common path for each circuit to exchange data.

In addition, a display unit 30 and an input unit 40 are connected to the bus line 16. The display unit 30 is, for example, a liquid crystal display. The display unit 30 displays a display screen (see reference numeral 30M in FIG. 3) on which a display region and a selection region are displayed, which will be described below. The display unit 30 may be a touch panel and may also be used as the input unit 40. The input unit 40 comprises, for example, a mouse and a keyboard and receives various setting inputs by the user. The input unit 40 according to this embodiment functions as an operation input unit that inputs an operation of selecting a plurality of examination images, which is received by the receiving unit 22.

Figure 3:
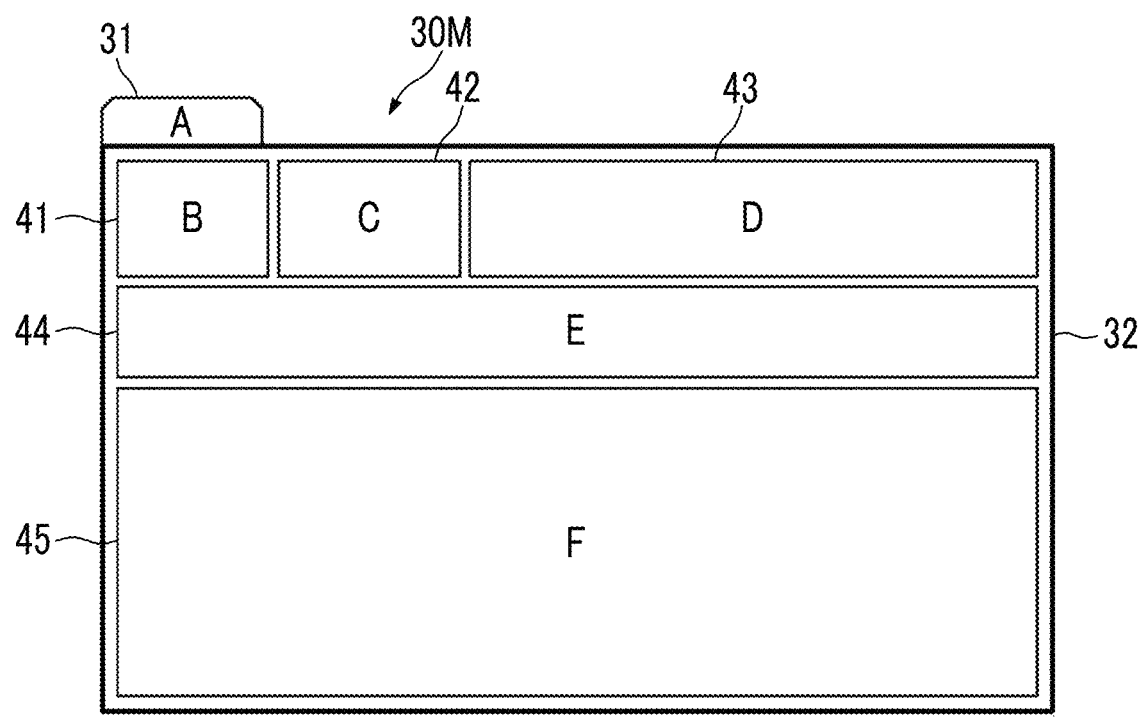
FIG. 3 is a diagram illustrating an example of a display screen according to an embodiment of the present disclosure.

The first display control unit 21 performs first display control to display, on the display screen, an examination image display region in which a plurality of examination images acquired for each examination are displayed and a thumbnail image display region in which a list of a plurality of thumbnail images obtained by reducing each of the plurality of examination images is displayed. The display screen 30M illustrated in FIG. 3 is an example of a display screen according to an embodiment of the present disclosure. The display screen 30M is an example of a graphical user interface (GUI) functioning as an operation screen that displays an examination image and various operation portions.

The display screen 30M includes a tab 31 represented by a region A, a patient information region 41 represented by a region B, an examination list region 42 represented by a region C, a thumbnail image display region 43 represented by a region D, a toolbar region 44 represented by a region E, and an image display region 45 represented by a region F as illustrated in FIG. 3. The image display region 45 corresponds to a display region according to the present disclosure and the thumbnail image display region 43 corresponds to a selection region according to the present disclosure.

Figure 4:
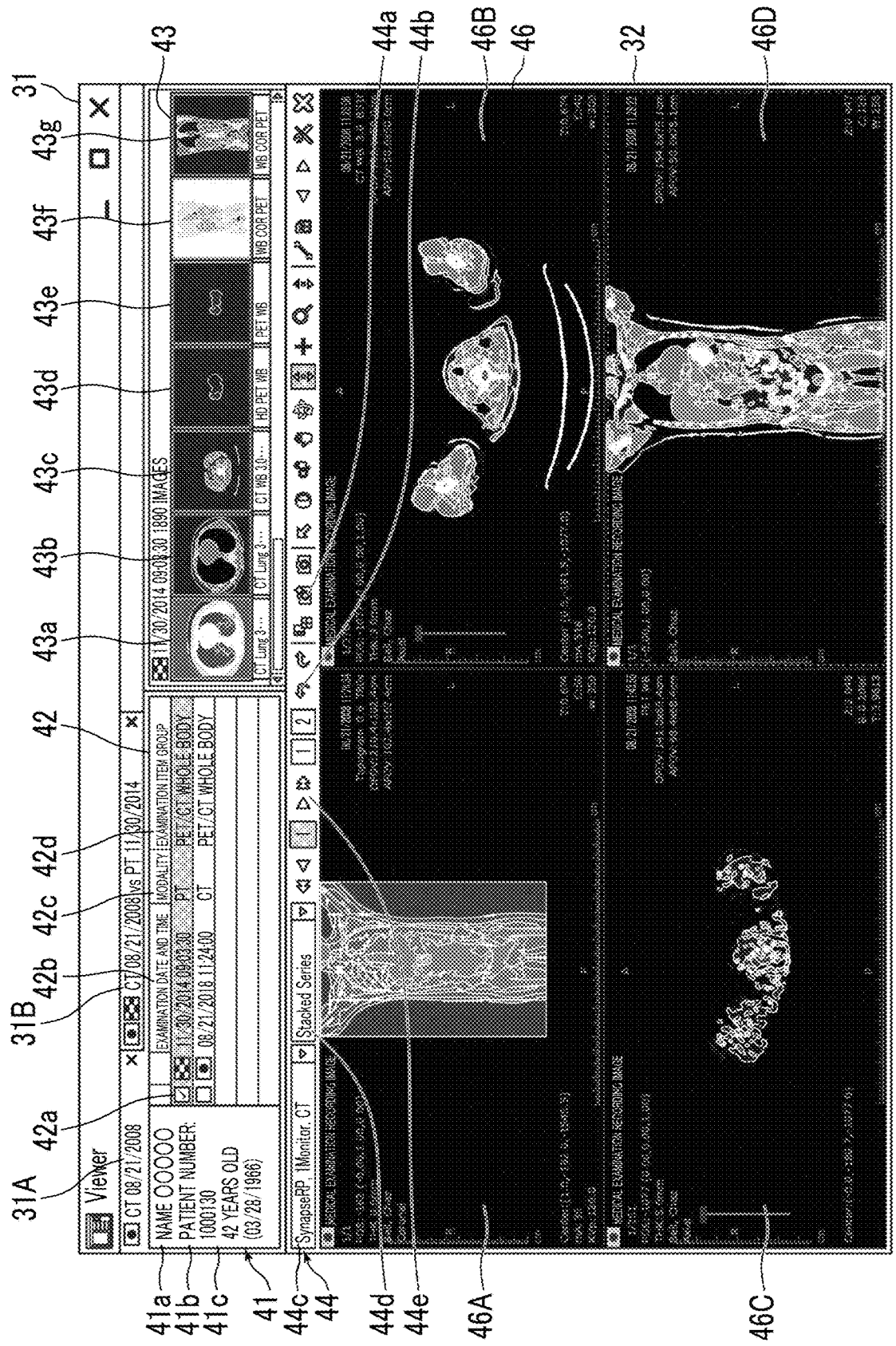
FIG. 4 is a diagram illustrating an example of the display of a display screen on a display unit according to a first embodiment of the present disclosure.

The tab 31 is an operation portion for switching a viewer region 32. In the display screen 30M illustrated in FIG. 3, only one tab 31 is provided. However, in a case in which there are a plurality of tabs 31 (tabs 31A and 31B) as illustrated in FIG. 4, the viewer regions 32 corresponding to each tab 31 are provided. As illustrated in FIG. 3, the viewer region 32 corresponding to the tab 31 includes the patient information region 41, the examination list region 42, the thumbnail image display region 43, the toolbar region 44, and the image display region 45.

FIG. 4 is a diagram illustrating an example of display on the display screen 30M of the display unit 30 according to an embodiment of the present disclosure. As illustrated in FIG. 4, the tab 31A and the tab 31B adjacent to the tab 31A are displayed on the display screen 30M and the display aspect of the viewer region 32 corresponding to the tab can be set for each tab. In FIG. 4, the viewer region 32 corresponding to the tab 31A is displayed on the display screen 30M.

A patient's name 41a, a patient number 41b, and a patient's age and birthday 41c are displayed in the patient information region 41. An examination list including a check box 42a, an examination date and time 42b, a modality 42c, an examination item group 42d, and a mark 42e is displayed in the examination list region 42.

The thumbnail image display region 43 is a region in which a thumbnail image obtained by reducing the examination image is displayed. In this embodiment, the thumbnail image display region 43 includes thumbnail regions 43a to 43g in which seven thumbnail images are displayed. The thumbnail images obtained by reducing the examination images acquired in the examination in which the check box 42a has been checked are displayed in the thumbnail regions 43a to 43g. In a case in which the number of examination images acquired in the examination is greater than seven, the first display control unit 21 operates, for example, a scroll bar illustrated in FIG. 4 to change the displayed thumbnail image.

Various command buttons, such as a snapshot button 44a, a return button 44b, a first pull-down menu 44c for selecting an arrangement configuration of the display screen 30M, and a second pull-down menu 44d for selecting the type of examination image acquired in one examination, are displayed in the toolbar region 44. In this embodiment, in a case in which the above-mentioned command button is pressed, a command associated with the pressed command button is input. Specifically, in a case in which the snapshot button 44a is pressed, a snapshot command is input. In a case in which the return button 44b is pressed, a command to return the image display region 45 to the previous display state is input.

The image display region 45 is a display region in which the examination images acquired for each examination are displayed. A plurality of display frames 46 that can be laid out as the display positions of a plurality of examination images are arranged in a grid shape in the image display region 45. In this embodiment, a total of four display frames 46A to 46D are arranged in two rows and two columns (2×2) and the examination images selected by the user are laid out and displayed in the four display frames 46A to 46D.

Figure 5:
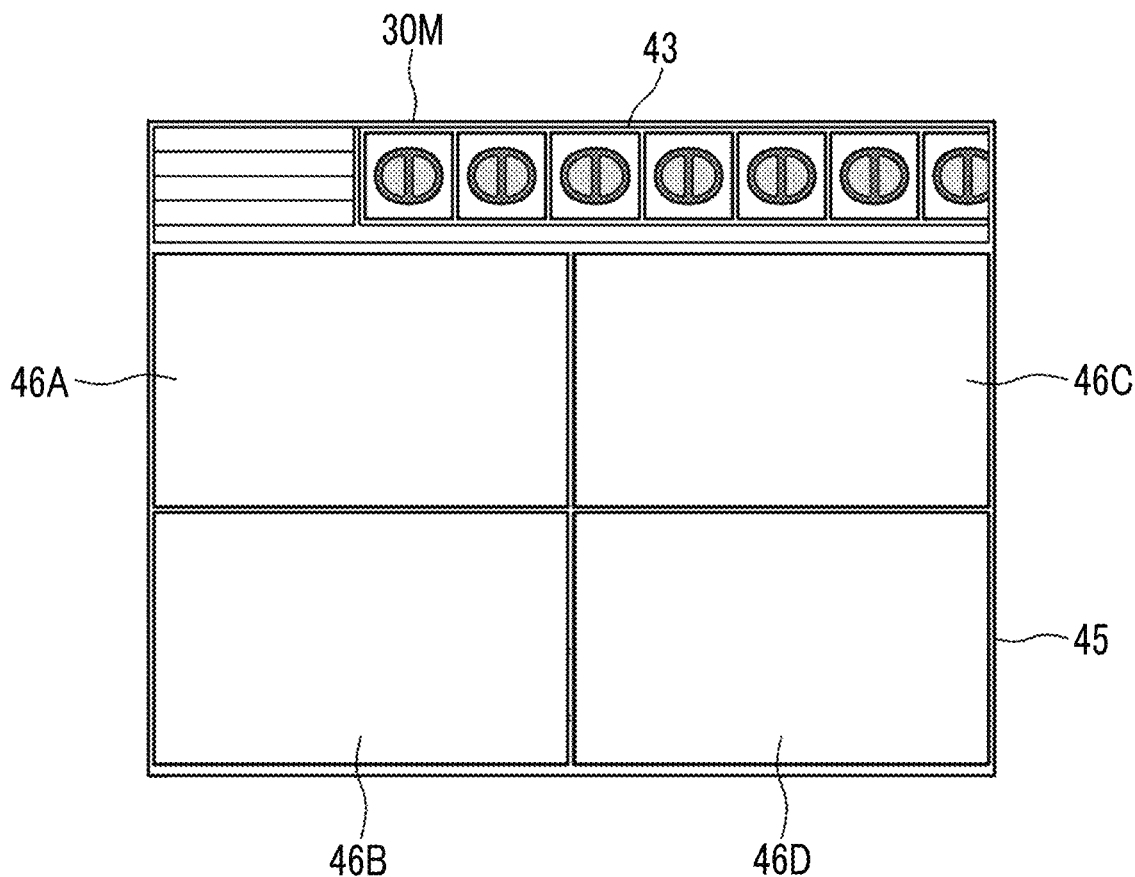
FIG. 5 is a diagram illustrating an example of the configuration of an image display region according to the first embodiment of the present disclosure.

In the image display region 45, the number of display frames 46 can be set in advance by the user. The arrangement configurations of the display frames 46 in the image display region 45 are stored as templates in the primary memory 12 and the user selects the arrangement configuration using, for example, the first pull-down menu 44c. FIG. 5 is a diagram illustrating an example of the configuration of the image display region 45 according to an embodiment of the present disclosure. For example, as illustrated in FIG. 5, the user selects the image display region 45 in which the display frames 46A to 46D are arranged in a 2×2 grid shape in advance. In the image display region 45, a frame line indicating the outer frame of the display frame 46 may be displayed such that the user can easily recognize the arrangement configuration of the display frame 46 or the frame line may not be displayed.

In this embodiment, the number and arrangement of display frames preset for each user are stored as initial display settings for each user in the secondary memory 13 and the stored initial display settings for each user are used at startup.

Figure 6:
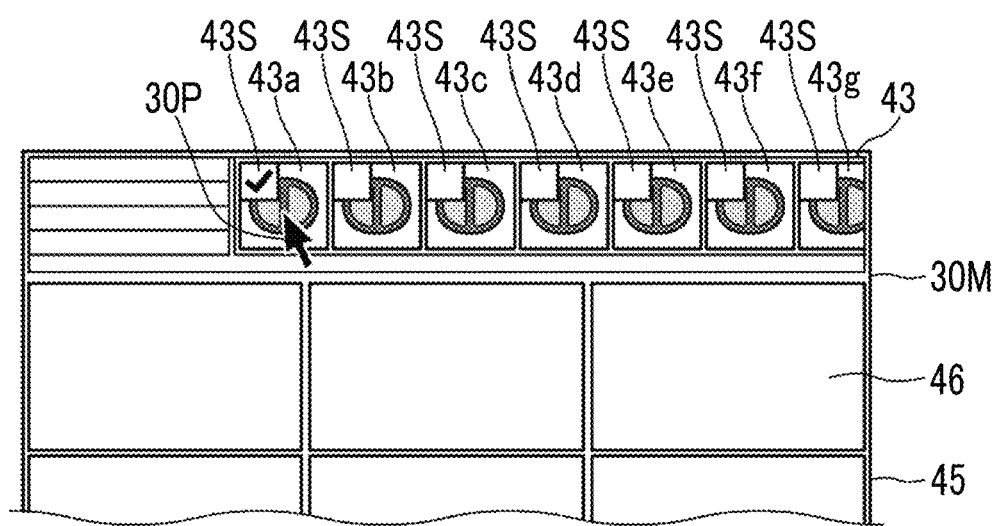
FIG. 6 is a diagram illustrating a thumbnail image selection operation.

Returning to FIG. 2, the receiving unit 22 receives an operation of selecting a plurality of thumbnail images from the thumbnail image display region 43 to select a plurality of examination images corresponding to the plurality of thumbnail images. FIG. 6 is a diagram illustrating a thumbnail image selection operation.

As illustrated in FIG. 6, check boxes 43S are displayed on the thumbnail images displayed in each of the thumbnail regions 43a to 43g in the thumbnail image display region 43. In a case in which the user operates the input unit 40 to move a pointer 30P and checks the check box 43S, the checked thumbnail image is selected. In a case in which a plurality of check boxes 43S are checked, a plurality of thumbnail images are selected. The receiving unit 22 receives an examination image corresponding to the selected thumbnail image as the selected examination image.

Figure 7:
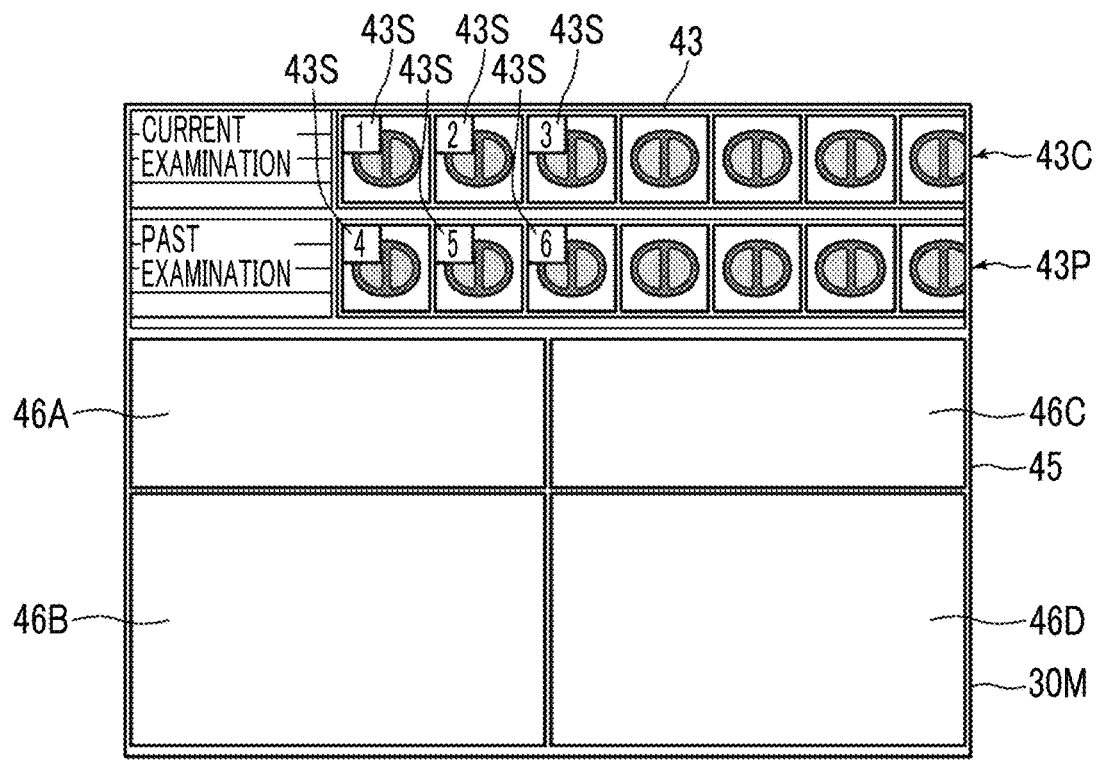
FIG. 7 is a diagram illustrating the reception of the selection of a plurality of thumbnail images.

FIG. 7 is a diagram illustrating the reception of the selection of a plurality of thumbnail images. For example, in the examination list region 42 illustrated in FIG. 4, the user checks the check boxes 42a of two examinations which are the same type and were made on different examination dates among the examination lists displayed in the examination list region 42. Then, as illustrated in FIG. 7, the first display control unit 21 displays a plurality of thumbnail images corresponding to a plurality of examination images acquired on two checked examination dates in the thumbnail image display region 43.

In this embodiment, it is assumed that, of the two checked examination dates, an examination performed on the most recent examination date is the current examination and an examination performed before the examination date on which the current examination was performed is the past examination. The first display control unit 21 displays a plurality of thumbnail images corresponding to a plurality of examination images acquired in the current examination in a current examination image display region 43C which is provided in an upper part of the thumbnail image display region 43. Further, the first display control unit 21 displays a plurality of thumbnail images corresponding to a plurality of examination images acquired in the past examination in a past examination image display region 43P which is provided in a lower part of the thumbnail image display region 43.

The receiving unit 22 receives, as the selected examination images, six examination images corresponding to a total of six thumbnail images, that is, three thumbnail images selected in the current examination image display region 43C and three thumbnail images selected in the past examination image display region 43P by the user. In addition, the first display control unit 21 displays numbers indicating the selection order on the selected thumbnail images in the order in which the check boxes 43S are checked.

The comparison unit 23 recognizes the number of examination images selected by the selection operation and compares the recognized number of selected examination images with the current number of display frames 46 in the image display region 45.

The change unit 24 changes the number of the display frames 46 on the basis of the comparison result of the comparison unit 23. Specifically, in a case in which the number of display frames is less than the number of selected examination images, the display frames 46 are added in the image display region 45 to change the number of display frames 46. The process of changing the number of display frames 46 will be described in detail below.

Figure 8:
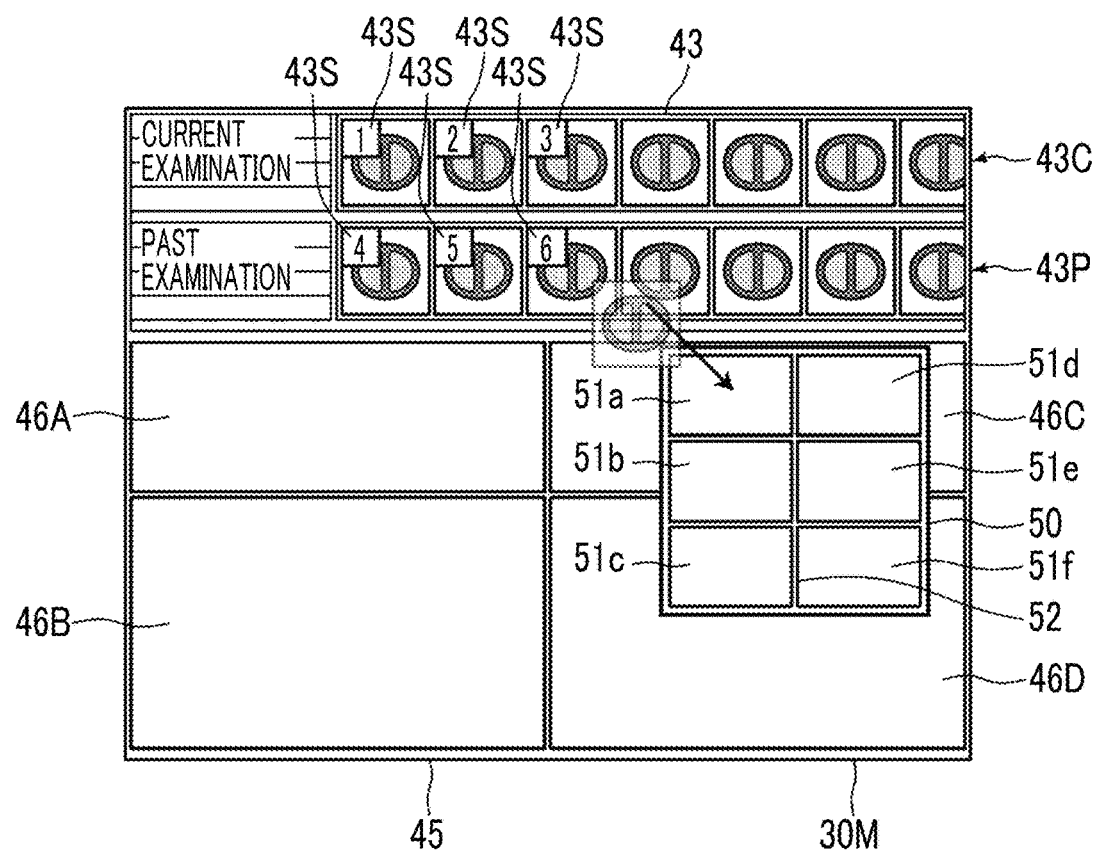
FIG. 8 is a diagram illustrating the display of a miniature window.

Also, in a miniature window in which miniature display frames 51 obtained by reducing the display frames 46 in the image display region 45 are arranged, the change unit 24 changes the number of miniature display frames 51 on the basis of the comparison result of the comparison unit 23, similarly to the image display region 45. FIG. 8 is a diagram illustrating the display of the miniature window 50.

As illustrated in FIG. 8, in the miniature window 50, the miniature display frames 51 obtained by reducing the grid-shaped arrangement of a plurality of display frames 46 are arranged in a grid shape. The miniature window 50 is displayed in the display screen 30M separately from the image display region 45. In this embodiment, since the number of selected examination images is six, six miniature display frames 51a to 51f are arranged in a grid shape of three rows and two columns (3×2) in the miniature window 50.

In the miniature window 50, frame lines 52 of the miniature display frames 51a to 51f are displayed. The miniature window 50 is disposed in the vicinity of the thumbnail image display region 43.

The second display control unit 25 perform is second display control to lay out the plurality of selected examination images in a plurality of display frames 46 equal to the number of selected examination images and to display the plurality of laid-out examination images on the display screen 30M.

In addition, the second display control unit 25 displays the miniature window 50, in which the miniature display frames 51 whose number is equal to the number of selected examination images are arranged, on the display screen 30M.

Figure 9:
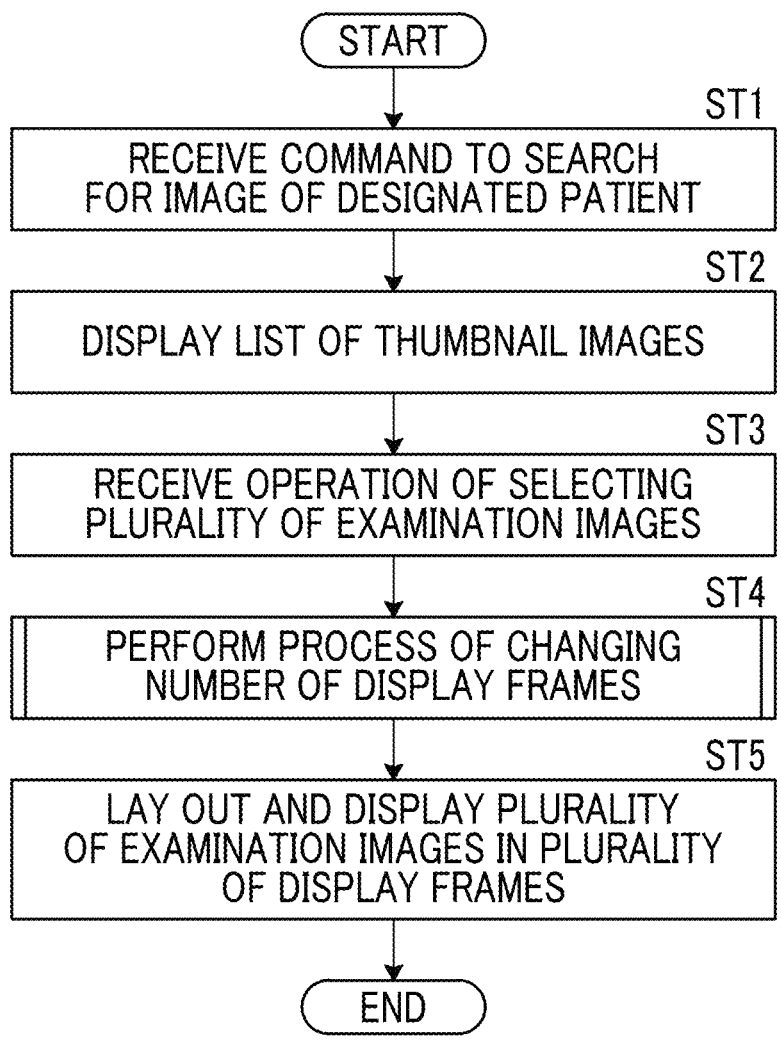
FIG. 9 is a flowchart illustrating a process performed in the first embodiment of the present disclosure.

Next, a process performed in this embodiment will be described. FIG. 9 is a flowchart illustrating a process performed in the first embodiment of the present disclosure. In this embodiment, in the image display region 45, the display frames 46A to 46D arranged in a 2×2 grid shape are set in advance.

First, the first display control unit 21 receives a command to search for the image of a designated patient (Step ST1). Specifically, as illustrated in FIG. 4, in a case in which the user inputs a patient ID using the input unit 40, the first display control unit 21 displays patient information corresponding to the input patient ID in the patient information region 41 of the display screen 30M. In addition, the first display control unit 21 displays a list of the examinations received by the input patient ID in the examination list region 42. Further, in a case in which the user checks the check box 42a of the examination list displayed in the examination list region 42, the first display control unit 21 searches for a plurality of examination images acquired on the checked examination date in the image storage server 3 and acquires the plurality of examination images.

In this embodiment, the first display control unit 21 acquires a plurality of examination images from the image storage server 3. However, the technology of the present disclosure is not limited thereto. The first display control unit 21 may acquire the examination images of the corresponding patient in advance from the image storage server 3, store the acquired examination images in the storage unit, search for a plurality of examination images acquired on the checked examination date from the plurality of examination images stored in the storage unit, and acquire the plurality of examination images. In addition, in this embodiment, the example in which the first display control unit 21 also functions as an image acquisition unit that acquires an examination image from the image storage server 3 has been described. However, of course, the image acquisition unit may be provided separately from the first display control unit 21.

Then, the first display control unit 21 displays a list of a plurality of thumbnail images obtained by reducing the plurality of acquired examination images in the thumbnail image display region 43 as illustrated in FIG. 4 (Step ST2).

Then, the receiving unit 22 receives an operation of selecting a plurality of thumbnail images from the list of the thumbnail images displayed in the thumbnail image display region 43 to select a plurality of examination images corresponding to the plurality of thumbnail images (Step ST3). In a case in which the user operates the input unit 40 to move the pointer 30P and checks the check boxes 43S of a plurality of thumbnail images that the user wants to select (see FIG. 6), the plurality of checked thumbnail images are selected (See FIG. 7).

In this embodiment, the receiving unit 22 receives, as the selected examination images, six examination images corresponding to a total of six thumbnail images, that is, three thumbnail images selected in the current examination image display region 43C and three thumbnail images selected in the past examination image display region 43P by the user.

Returning to FIG. 9, then, the second display control unit 25 performs a process of changing the number of display frames 46 in the image display region 45 (Step ST4).

Figure 10:
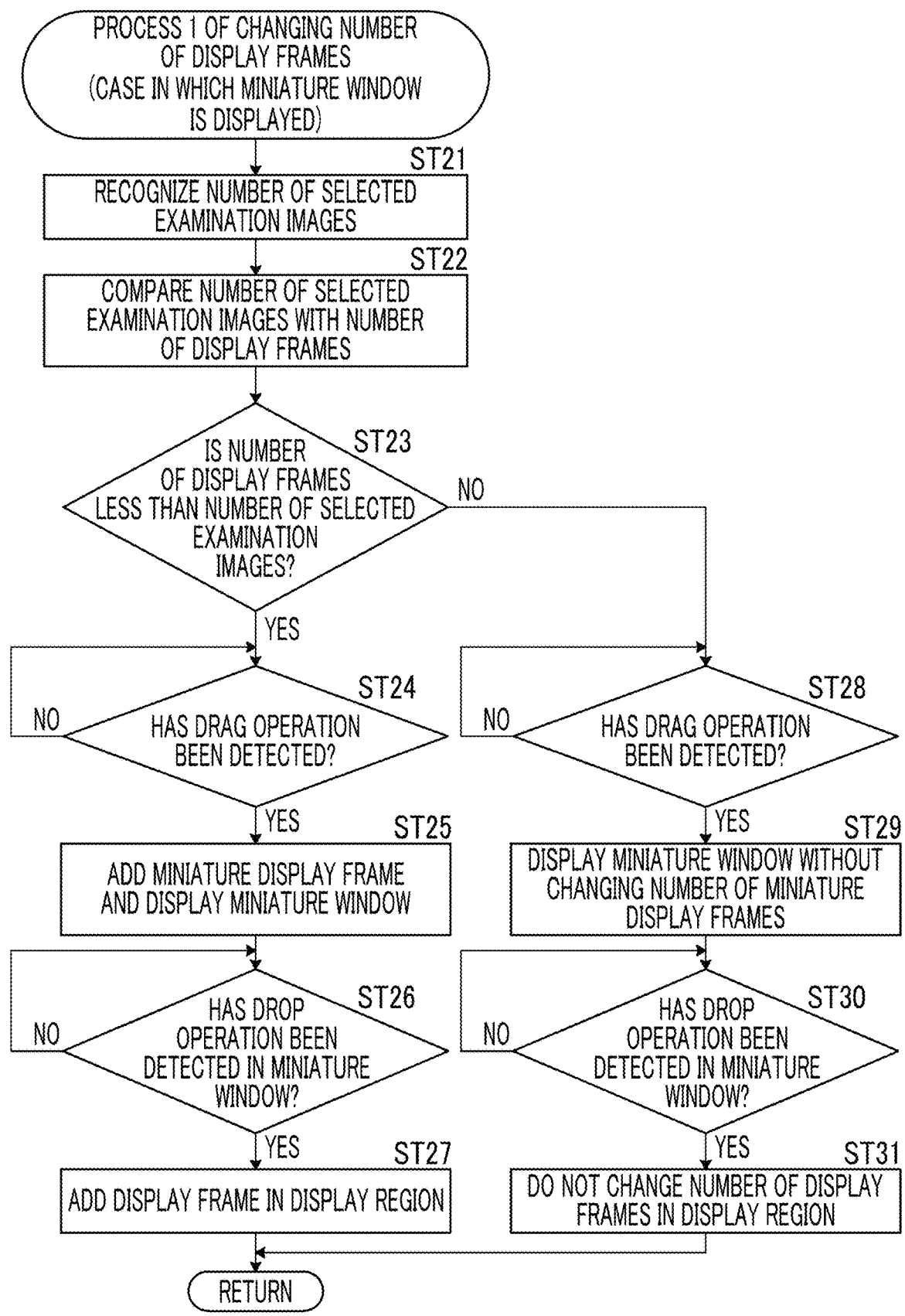
FIG. 10 is a flowchart illustrating a series of processes for changing the number of display frames in a case in which the miniature window is displayed.

FIG. 10 is a flowchart illustrating a series of processes for changing the number of display frames 46 in a case in which the miniature window 50 is displayed. As illustrated in FIG. 10, first, the comparison unit 23 recognizes the number of examination images selected by the selection operation (Step ST21). Then, the comparison unit 23 compares the recognized number of selected examination images with the current number of display frames 46 in the image display region 45 (Step ST22).

In a case in which the current number of display frames 46 is less than the recognized number of selected examination images (Step ST23; NO), it is detected whether or not a drag operation of dragging a plurality of thumbnail images selected in the thumbnail image display region 43 from the thumbnail image display region 43 has been performed (Step ST24). The detection of the drag operation can be performed, for example, by detecting whether or not the mouse has been moved in a state in which the left button of the mouse is pressed on any region of the plurality of selected thumbnail images.

In a case in which the detection result in Step ST24 is "NO" (Step ST24; NO), the process in Step ST24 is repeated until the second display control unit 25 detects a drag operation. In a case in which the detection result in Step ST24 is "YES" (Step ST24; YES), the change unit 24 adds the miniature display frame 51 and the second display control unit 25 displays, on the display screen 30M, the miniature window 50 in which the miniature display frames 51 whose number is equal to the number of selected examination images are arranged (Step ST25).

Similarly to four display frames 46A to 46D arranged in a 2×2 grid shape which is set in advance in the image display region 45, four miniature display frames 51a to 51d arranged in a 2×2 grid shape are set as initial settings in the miniature window 50.

In this embodiment, the number of the selected examination images is six. Since the number of display frames 46 set in advance in the image display region 45 is four, it is difficult to lay out the six selected examination images. Therefore, first, before the display frames 46 of the image display region 45 are added, the miniature display frames 51 are added according to the number of selected examination images.

In the miniature window 50 displayed on the display screen 30M, as illustrated in FIG. 8, six miniature display frames 51a to 51f are arranged in a grid shape of three rows and two columns (3×2).

Then, in a case in which the miniature window 50 is displayed on the display screen 30M, the second display control unit 25 detects whether or not a drop operation has been performed in the miniature window 50 (Step ST26). In a case in which a plurality of thumbnail images selected in the thumbnail image display region 43 have been dragged in the direction of an arrow in FIG. 8 and then dropped in the miniature window 50 as illustrated in FIG. 8, the second display control unit 25 detects that a drop operation has been performed.

In a case in which the detection result in Step ST26 is "NO" (Step ST26; NO), the process in Step ST26 is repeated until the second display control unit 25 detects a drop operation. In a case in which the detection result in Step ST26 is "YES" (Step ST26; YES), the second display control unit 25 adds the display frame 46 of the image display region 45 (Step ST27).

In the image display region 45, four display frames 46A to 46D arranged in a 2×2 grid shape are set in advance. However, in this embodiment, since the number of selected examination images is six, it is difficult to lay out the selected examination images in the display frames 46A to 46D. Therefore, the second display control unit 25 adds two display frames to the image display region 45 according to six selected examination images to set six display frames.

Figure 11:
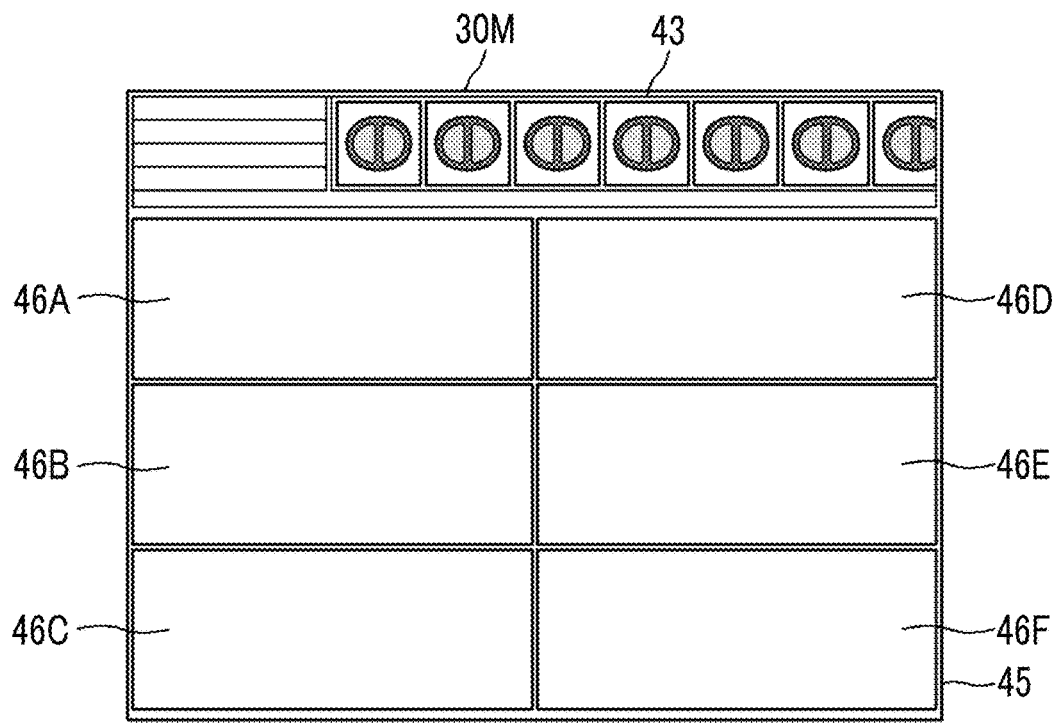
FIG. 11 is a diagram illustrating an example of the display of the display screen after the number of display frames is changed.

FIG. 11 is a diagram illustrating an example of the display of the display screen after the number of display frames is changed.

The second display control unit 25 adds two display frames 46E and 46F to the four display frames 46A to 46D arranged in a 2×2 grid shape in advance in the image display region 45 to set the display frames 46A to 46F arranged in a 3×2 grid shape as illustrated in FIG. 11.

On the other hand, in a case in which the current number of display frames 46 is equal to or greater than the recognized number of selected examination images in Step ST23 (Step ST23; YES), it is detected whether or not a drag operation of dragging a plurality of thumbnail images selected in the thumbnail image display region 43 from the thumbnail image display region 43 has been performed (Step ST28). In a case in which the detection result in Step ST28 is "NO" (Step ST28; NO), the process in Step ST28 is repeated until the second display control unit 25 detects a drag operation. In a case in which the detection result in Step ST28 is "YES" (Step ST28; YES), the second display control unit 25 determines that the current number of display frames 46 is equal to or greater than the recognized number of selected examination images and displays the initial settings, that is, the miniature window 50 in which four miniature display frames 51a to 51d are arranged on the display screen 30M, without changing the number of miniature display frames 51 (Step ST29).

Then, in a case in which the miniature window 50 is displayed on the display screen 30M, the second display control unit 25 detects whether or not a drop operation has been performed in the miniature window 50 (Step ST30). In a case in which the detection result in Step ST30 is "NO" (Step ST30; NO), the process in Step ST30 is repeated until the second display control unit 25 detects a drop operation. In a case in which the detection result in Step ST30 is "YES" (Step ST30; YES), the second display control unit 25 does not change the number of display frames 46 in the image display region 45 since it has been determined in Step ST23 that the current number of display frames 46 is equal to or greater than the recognized number of selected examination images (Step ST31).

In this embodiment, four display frames 46A to 46D arranged in a 2×2 grid shape are set in advance in the image display region 45. Therefore, the four display frames 46A to 46D are set without any change.

Figure 12:
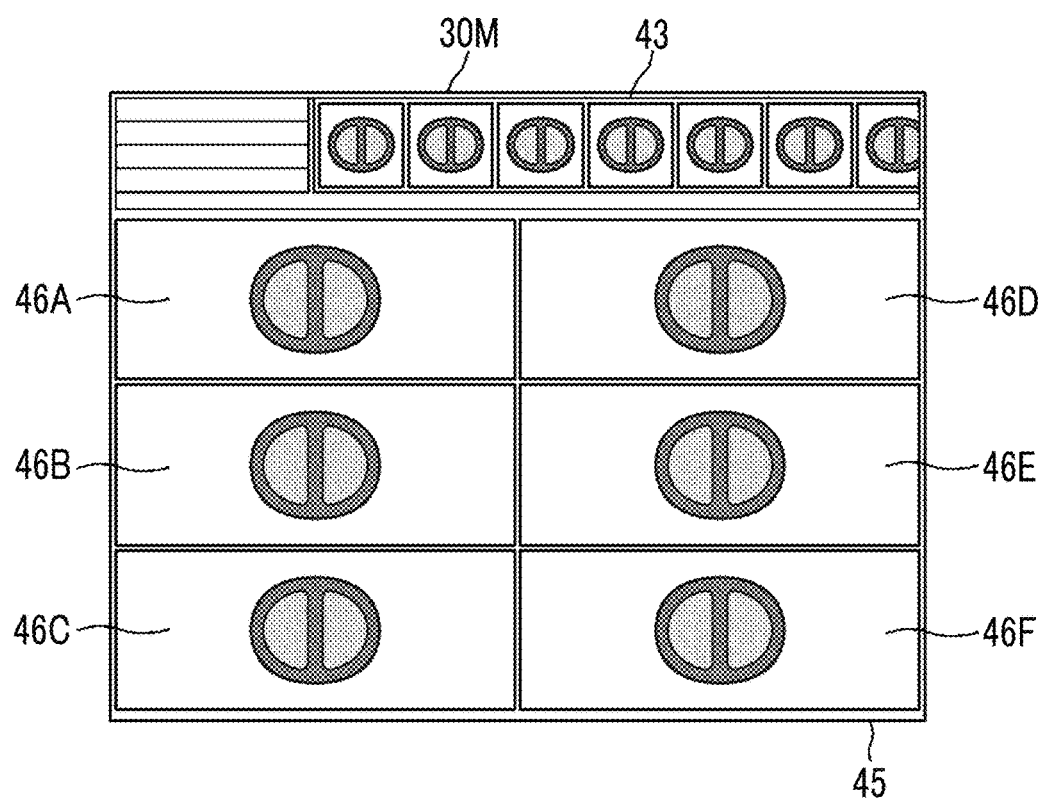
FIG. 12 is a diagram illustrating an example of the display of the display screen in a case in which examination images are laid out in the display frames after the number of display frames is changed.

Then, returning to FIG. 9, the second display control unit 25 lays out a plurality of examination images in the display frames 46 of the image display region 45 and displays the plurality of examination images laid out in the display frames 46 on the display screen 30M (Step ST5). FIG. 12 is a diagram illustrating an example of the display of the display screen 30M in a case in which examination images are laid out in the display frames after the number of display frames is changed.

As illustrated in FIG. 12, the second display control unit 25 lays out six examination images received by the receiving unit 22 in the display frames 46A to 46F on the basis of the arrangement order given to the thumbnail images corresponding to each of the examination images. That is, the second display control unit 25 lays out the examination images in the order displayed in the check boxes 43S of the thumbnail image display region 43 (see FIG. 7). In a case in which six examination images are laid out in the display frames 46A to 46F, the examination images are laid out in the arrangement direction set by the user in advance.

In this embodiment, the arrangement direction is set as the vertical direction. Therefore, first, the second display control unit 25 lays out three examination images (see FIG. 7) acquired by the current examination in the order of 1, 2, and 3 in the display frame 46A, the display frame 46B, and the display frame 46C, respectively. Then, the second display control unit 25 lays out three examination images (see FIG. 7) acquired by the past examination in the order of 4, 5, and 6 in the display frame 46D, the display frame 46E, and the display frame 46F, respectively.

The second display control unit 25 displays six examination images laid out in the six display frames 46A to 46F on the display screen 30M.

As described above, according to the first embodiment, in a case in which a plurality of examination images are laid out in a plurality of display frames 46 arranged in the image display region 45 and the number of display frames 46 is less than the number of selected examination images, the number of display frames 46 is changed to be equal to the number of examination images. Therefore, it is possible to reduce the trouble of the user, as compared to a case in which the user resets the number of display frames whenever it is difficult to arrange a plurality of selected examination images in the display frames. As a result, user operability is improved.

In the first embodiment, in a case in which the examination image of the next patient is interpreted, that is, the next patient ID is interpreted after the number of display frames 46 and arrangement thereof are changed from the initial settings, the number of display frames 46 and the arrangement thereof are returned to the initial settings.

In the first embodiment, the display frames 46 are added to be equal to the number of selected examination images. However, the technology of the present disclosure is not limited thereto. For example, in a case in which the number of selected examination images is an odd number, the number of display frames 46 does not necessarily need to be equal to the number of selected examination images. Specifically, in a case in which the current number of display frames 46 is two and the number of selected examination images is three, two display frames 46 may be added such that four display frames 46 are arranged. Therefore, the display frames 46 can be arranged in a 2×2 grid shape on the display screen 30M, which makes it easy to perform comparative interpretation.

Further, according to the first embodiment, in a state in which a plurality of thumbnail images are selected in the thumbnail image display region 43 and before the same number of display frames as the number of selected examination images is laid out in the image display region 45, the second display control unit 25 displays the same number of miniature display frames 51 as the number of selected examination images in the miniature window 50. Therefore, before the examination images are laid out in the image display region 45, it is possible to visually recognize the arrangement configuration of the display frames 46 after the display frames are changed. As a result, it is possible to check whether or not the number of selected examination images (thumbnail images) is a desired number before the examination images are displayed.

In the first embodiment, the miniature window 50 is displayed before the same number of display frames as the number of selected examination images is laid out in the image display region 45. However, the technology of the present disclosure is not limited thereto. Before the miniature window 50 is displayed or at the same time as the miniature window 50 is displayed, the same number of display frames 46 as the number of selected examination images may be laid out in the image display region 45. Here, in the present disclosure, the term "at the same time" is synonymous with laying out the same number of display frames 46 as the number of selected examination images in synchronization with the display of the miniature window 50.

In the first embodiment, the miniature window 50 is not displayed before a plurality of thumbnail images are selected and is displayed in a case in which a plurality of thumbnail images are selected in the thumbnail image display region and then the drag of the plurality of selected thumbnail images is started. Therefore, in a case in which a large number of thumbnail images are displayed, that is, the thumbnail image display region is large and the thumbnail image is selected, the miniature window 50 is not displayed. Therefore, the selection of the thumbnail image is not hindered.

According to the first embodiment, the number of display frames 46 and the arrangement thereof which have been set in advance for each user are used as the initial display settings for each user at startup. Therefore, it is not necessary to change the setting of the layout whenever the system starts up. As a result, user operability is improved.

Further, according to the first embodiment, the arrangement order desired by the user can be determined by the selection order of the thumbnail images. Therefore, it is possible to reduce the time and effort required for setting the arrangement order and user operability is improved.

Furthermore, according to the first embodiment, since the command to lay out the examination images in the display frames 46 is received by the drag and drop method, the user can perform the command operation with one operation. Therefore, operability is high. In this embodiment, the example in which the command operation is received by the drag and drop method has been described. However, the technology of the present disclosure is not limited thereto. The command operation may be received by aspects other than the drag and drop method. For example, after selecting a thumbnail image, the user may perform designation by clicking a desired position using the pointer 30P displayed on the display screen 30M.

Further, according to the first embodiment, the miniature window 50 is disposed in the vicinity of the thumbnail image display region 43. Therefore, the user may drag the thumbnail image by a short distance as compared to a case in which the user performs the command operation using the image display region 45. Therefore, operability is improved. Here, the term "vicinity" means a position where the drag distance of the selected thumbnail image from the thumbnail image display region 43 to the miniature window 50 is shorter than the drag distance of the selected thumbnail image from the thumbnail image display region 43 to the image display region 45. Examples of a specific display position of the miniature window 50 include a position where a part of the miniature window 50 overlaps the thumbnail image display region 43 and a position where the lower side of the miniature window 50 overlaps the upper side of the image display region 45.

In the first embodiment, the miniature window 50 is displayed on the display screen 30M at the timing when the drag operation is detected, that is, at the timing when the drag operation is started. However, the technology of the present disclosure is not limited thereto. For example, the miniature window 50 may be displayed on the display screen 30M immediately before the drag operation is started, specifically, at the timing when the left button of the mouse is pressed on any region of a plurality of thumbnail images.

In the first embodiment, in the image display region 45, a plurality of display frames 46 that can be laid out as the display positions of a plurality of examination images are arranged in a grid shape. In the technology of the present disclosure, the term "arrangement in a grid shape" includes, for example, a case in which the display frames 46 are arranged in one row and four columns (1×4) or in four rows and one column (4×1).

Figure 13:
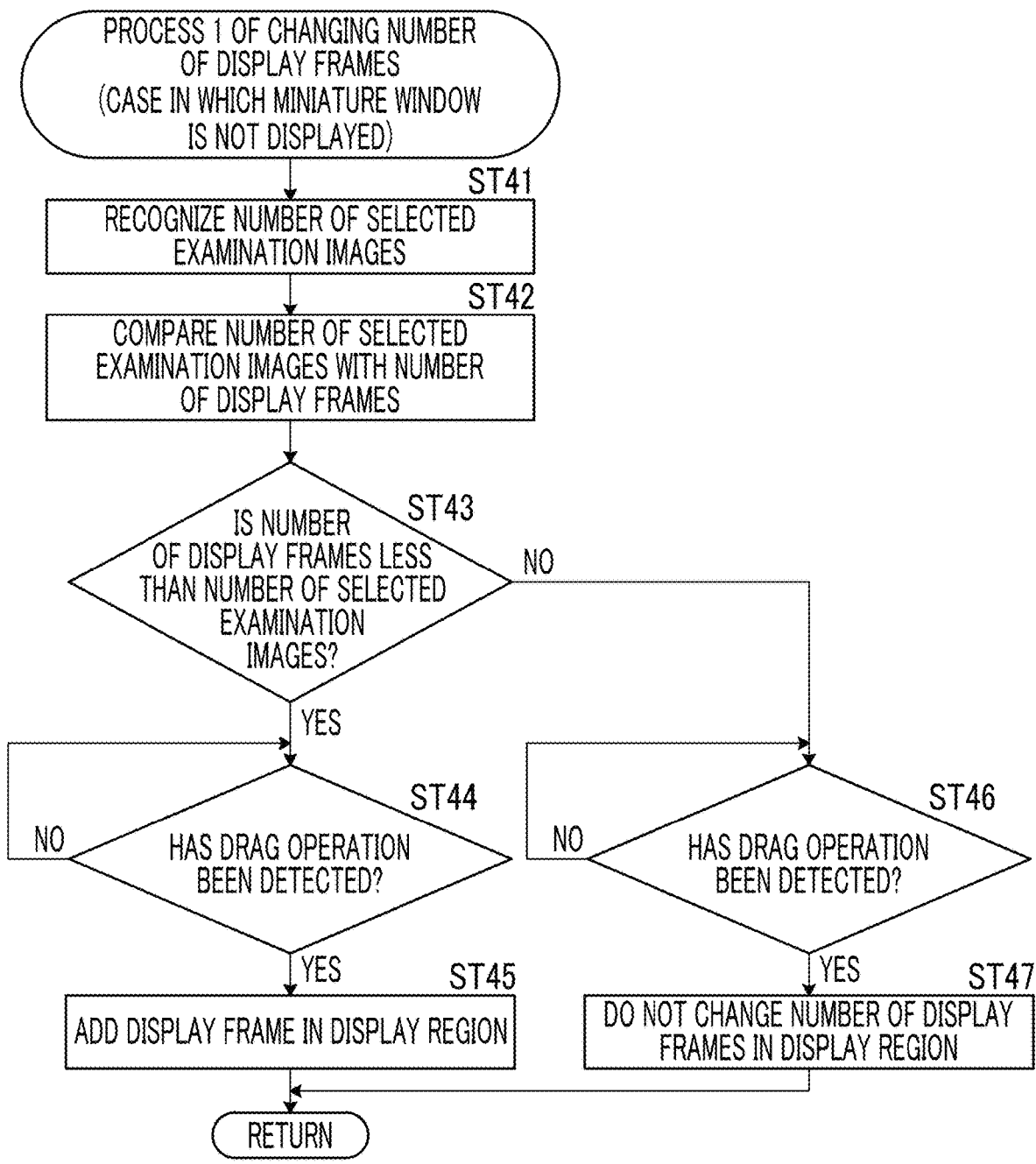
FIG. 13 is a flowchart illustrating a series of processes for changing the number of display frames in a case in which the miniature window is not displayed.

Next, a second embodiment of the present disclosure will be described. In the first embodiment, the miniature window 50 is displayed. However, in the second embodiment, the miniature window 50 is not displayed. The method in which the miniature window 50 is not displayed differs from that in the first embodiment in the process of changing the number of display frames 46 in Step ST4 of the flowchart illustrated in FIG. 9. Since processes other than Step ST4 are the same as those in FIG. 9, the description thereof will not be repeated. FIG. 13 is a flowchart illustrating a series of processes for changing the number of display frames 46 in a case in which the miniature window 50 is not displayed.

As illustrated in FIG. 13, first, the comparison unit 23 recognizes the number of examination images selected by a selection operation (Step ST41). Then, the comparison unit 23 compares the recognized number of selected examination images with the current number of display frames 46 in the image display region 45 (Step ST42).

In a case in which the current number of display frames 46 is less than the recognized number of selected examination images (Step ST43; NO), it is detected whether or not a drag operation of dragging a plurality of thumbnail images selected in the thumbnail image display region 43 from the thumbnail image display region 43 has been performed (Step ST44).

In a case in which the detection result in Step ST44 is "NO" (Step ST44; NO), the process in Step ST44 is repeated until the second display control unit 25 detects a drag operation. In a case in which the detection result in Step ST44 is "YES" (Step ST44; YES), the second display control unit 25 adds the display frames 46 of the image display region 45 (Step ST45).

Specifically, for example, as in the first embodiment, in a case in which six examination images are selected, the image display region 45 is changed from the initial setting display (see FIG. 5) in which four display frames 46A to 46D are arranged in a 2×2 grid shape to the display in which six display frames 46A to 46F are arranged in a 3×2 grid shape.

On the other hand, in a case in which the current number of display frames 46 is equal to or greater than the recognized number of selected examination images in Step ST43 (Step ST43; YES), it is detected whether or not a drag operation of dragging a plurality of thumbnail images selected in the thumbnail image display region 43 from the thumbnail image display region 43 has been performed (Step ST46).

In a case in which the detection result in Step ST46 is "NO" (Step ST46; NO), the process in Step ST46 is repeated until the second display control unit 25 detects a drag operation. In a case in which the detection result in Step ST46 is "YES" (Step ST46; YES), the second display control unit 25 does not change the number of display frames 46 in the image display region 45 since it has been determined in Step ST43 that the current number of display frames 46 is equal to or greater than the recognized number of selected examination images (Step ST47).

In this embodiment, four display frames 46A to 46D arranged in a 2×2 grid shape are set in advance in the image display region 45. Therefore, the four display frames 46A to 46D are set without any change.

Then, in a case in which the process in Step ST45 or Step ST47 ends, the process of changing the number of display frames 46 ends. Then, the process proceeds to Step ST5 illustrated in FIG. 9.

In the second embodiment, the miniature window 50 is not displayed and the image display region 45 in which the number of display frames 46 is changed according to the number of selected examination images is displayed on the display screen 30M. Therefore, in the second embodiment, since the miniature window 50 is not displayed, it is possible to prevent the image display region 45 from being hidden by the miniature window 50. This makes it easy to check the arrangement configuration of a plurality of display frames 46 in the image display region 45.

Next, a third embodiment of the present disclosure will be described. In the first embodiment, the number of display frames 46 is not changed in a case in which the number of display frames 46 is equal to or greater than the recognized number of selected examination images. However, in the third embodiment, in the number of display frames 46 is greater than the recognized number of selected examination images, the number of display frames 46 is deleted. A method of deleting the display frame 46 differs from that in the first embodiment in the process of changing the number of display frames 46 in Step ST4 of the flowchart illustrated in FIG. 9. Since processes other than Step ST4 are the same as those in FIG. 9, the description thereof will not be repeated.

Figure 14:
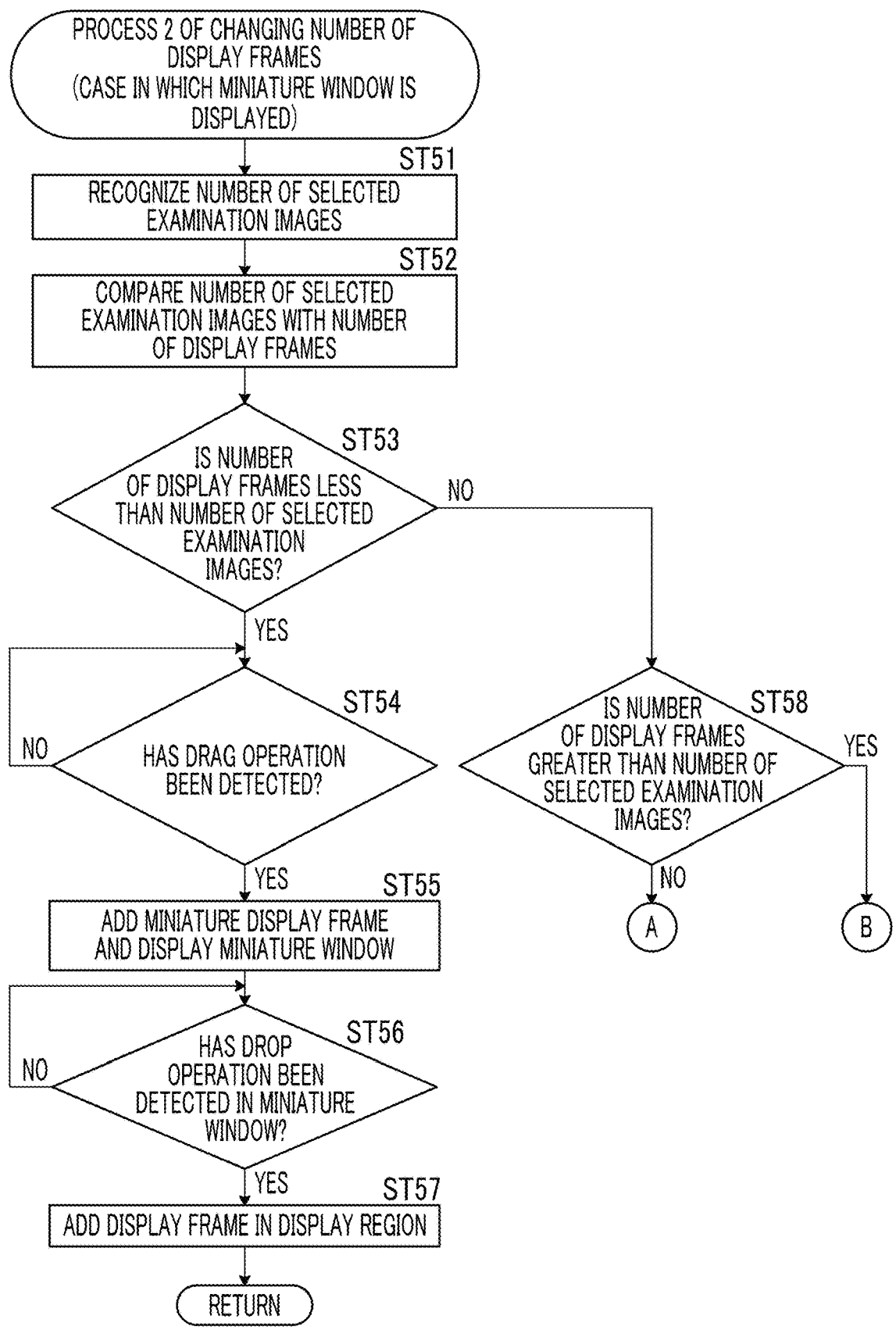
FIG. 14 is another flowchart illustrating a series of processes for changing the number of display frames in a case in which the miniature window is displayed.

FIG. 14 is a flowchart illustrating a series of processes for changing the number of display frames 46 in a case in which the miniature window 50 is displayed. In FIG. 14, a process in a case in which the number of display frames 46 is less than the recognized number of selected examination images, that is, a process in Steps ST51 to ST57 is the same as the process in Steps ST21 to ST27 illustrated in FIG. 10. Therefore, the description thereof will not be repeated.

As illustrated in FIG. 14, the process proceeds to A in a case in which the current number of display frames 46 is equal to or greater than the recognized number of selected examination images (Step ST53; NO) and the current number of display frames 46 is equal to or less than the recognized number of selected examination images (Step ST58; NO), that is, in a case in which the current number of display frames 46 is equal to the recognized number of selected examination images.

Figure 15:
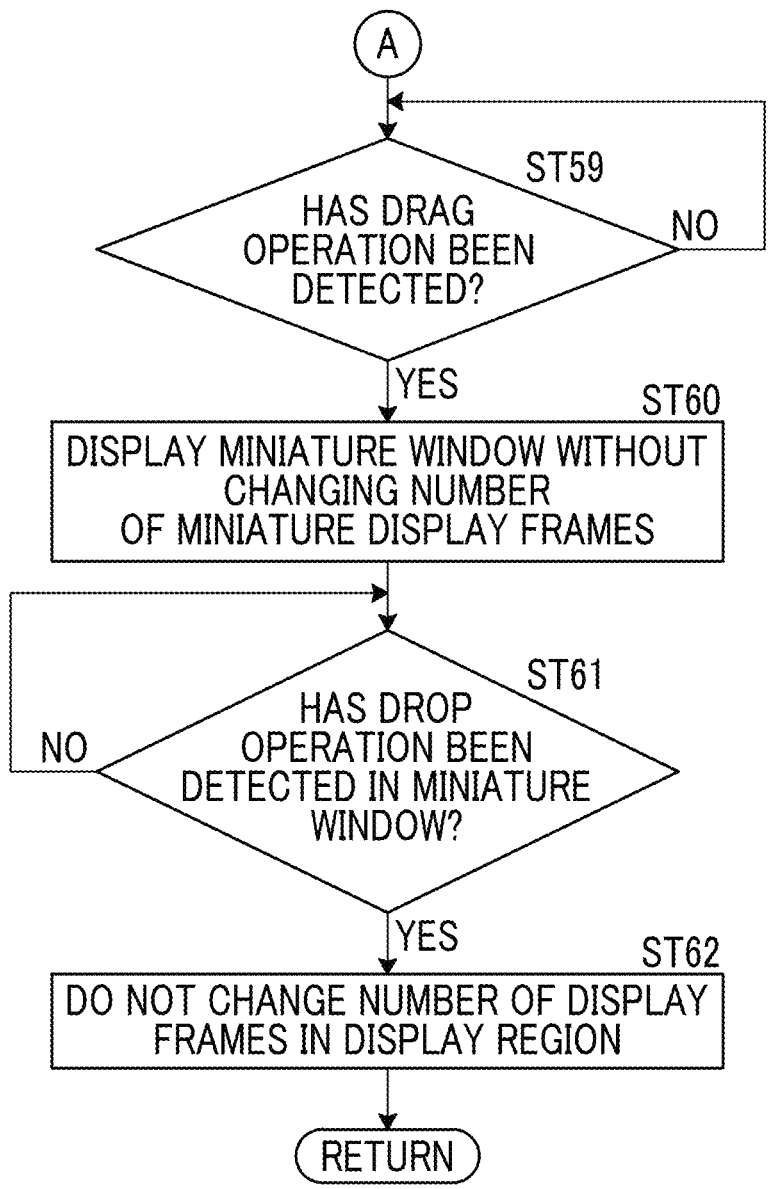
FIG. 15 is a flowchart illustrating a process after A in FIG. 14.

FIG. 15 is a flowchart illustrating a process after A in FIG. 14. In a case in which the determination result in Step ST58 is "NO", that is, in a case in which the current number of display frames 46 is equal to the recognized number of selected examination images (Step ST58; NO), it is detected whether or not a drag operation of dragging a plurality of thumbnail images selected in the thumbnail image display region 43 from the thumbnail image display region 43 has been performed (Step ST59). In a case in which the detection result in Step ST59 is "NO" (Step ST59; NO), the process in Step ST59 is repeated until the second display control unit 25 detects a drag operation. In a case in which the detection result in Step ST59 is "YES" (Step ST59; YES), the second display control unit 25 determines that the current number of display frames 46 is equal to the recognized number of selected examination images and displays the initial settings, that is, the miniature window 50 in which four miniature display frames 51a to 51d are arranged on the display screen 30M, without changing the number of miniature display frames 51 (Step ST60).

Then, in a case in which the miniature window 50 is displayed on the display screen 30M, the second display control unit 25 detects whether or not a drop operation has been performed in the miniature window 50 (Step ST61). In a case in which the detection result in Step ST61 is "NO" (Step ST61; NO), the process in Step ST61 is repeated until the second display control unit 25 detects a drop operation. In a case in which the detection result in Step ST61 is "YES" (Step ST61; YES), the second display control unit 25 does not change the number of display frames 46 in the image display region 45 since it has been determined in Step ST58 that the current number of display frames 46 is equal to the recognized number of selected examination images (Step ST62).

Returning to FIG. 14, the process proceeds to B in a case in which the determination result in Step ST58 is "YES", that is, in a case in which the current number of display frames 46 is greater than the recognized number of selected examination images (Step ST58; YES).

Figure 16:
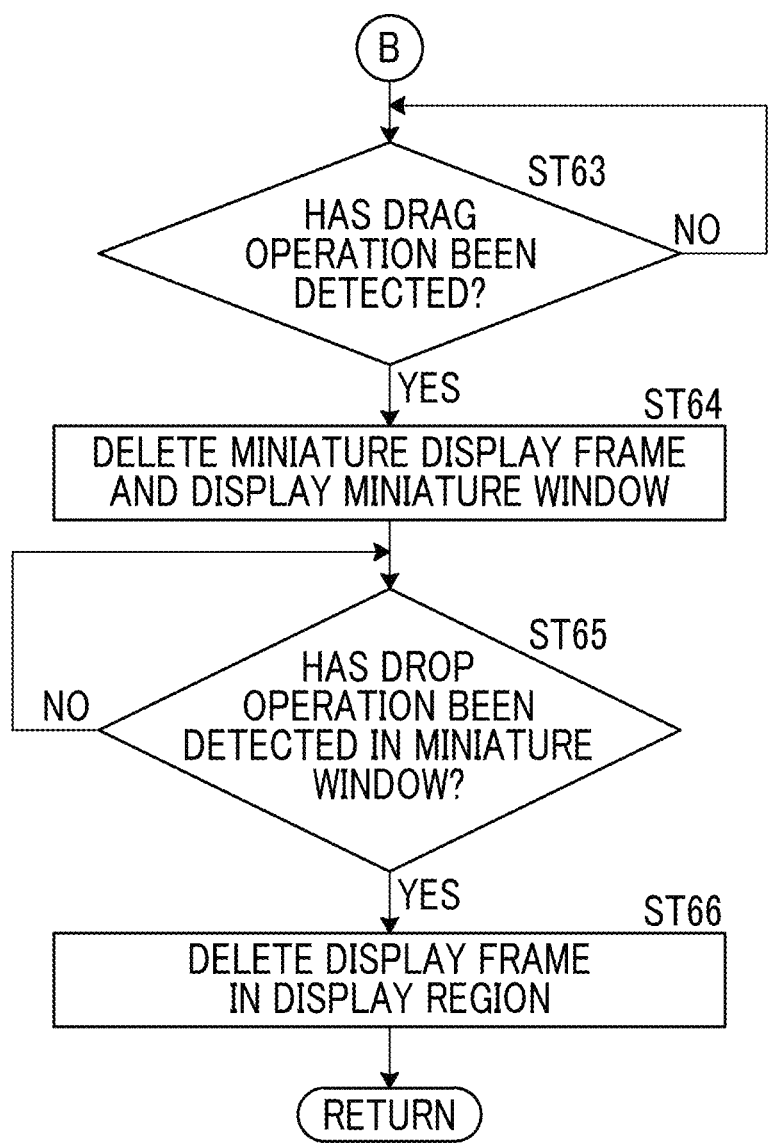
FIG. 16 is a flowchart illustrating a process after B in FIG. 14.

FIG. 16 is a flowchart illustrating a process after B illustrated in FIG. 14. In a case in which the determination result in Step ST58 is "YES", that is, in a case in which the current number of display frames 46 is greater than the recognized number of selected examination images (Step ST58; YES), it is detected whether or not a drag operation of dragging a plurality of thumbnail images selected in the thumbnail image display region 43 from the thumbnail image display region 43 has been performed (Step ST63).

In a case in which the detection result in Step ST63 is "NO" (Step ST63; NO), the process in Step ST63 is repeated until the second display control unit 25 detects a drag operation. In a case in which the detection result in Step ST63 is "YES" (Step ST63; YES), the second display control unit 25 determines that the current number of display frames 46 is greater than the recognized number of selected examination images and deletes the miniature display frame 51. Then, the second display control unit 25 displays, on the display screen 30M, the miniature window 50 in which the same number of miniature display frames 51 as the number of the selected examination images is arranged (Step ST64).

Then, in a case in which the miniature window 50 is displayed on the display screen 30M, the second display control unit 25 detects whether or not a drop operation has been performed in the miniature window 50 (Step ST65). In a case in which the detection result in Step ST65 is "NO" (Step ST65; NO), the process in Step ST65 is repeated until the second display control unit 25 detects a drop operation. In a case in which the detection result in Step ST65 is "YES" (Step ST65; YES), the second display control unit 25 deletes the display frames 46 such that the number of display frames 46 in the image display region 45 is equal to the number of selected examination images since it has been determined in Step ST58 that the current number of display frames 46 is greater than the recognized number of selected examination images (Step ST66).

As described above, according to the third embodiment, in a case in which a plurality of examination images are laid out in a plurality of display frames 46 arranged in the image display region 45 and the number of display frames 46 is greater than the number of selected examination images, the number of display frames 46 is changed to be equal to the number of examination images. Therefore, it is possible to delete the display frame 46 in which the selected examination image is not disposed. Therefore, one display frame 46 can be set to have a large size in the image display region 45, as compared to a case in which the display frame 46 in which the selected examination image is not disposed is set. As a result, the examination image can be easily interpreted on the display screen 30M.

In the third embodiment, the display frames 46 are deleted such that the number of display frames 46 is equal to the number of selected examination images. However, the technology of the present disclosure is not limited thereto. For example, in a case in which the number of selected examination images is an odd number, the number of display frames 46 does not necessarily need to be equal to the number of selected examination images. Specifically, in a case in which the current number of display frames 46 is six and the number of selected examination images is three, two display frames 46 may be deleted such that four display frames 46 are arranged. Therefore, the display frames 46 can be arranged in a 2×2 grid shape on the display screen 30M, which makes it easy to perform comparative interpretation.

Next, a fourth embodiment of the present disclosure will be described. In the second embodiment, the number of display frames 46 is not changed in a case in which the number of display frames 46 is equal to or greater than the recognized number of selected examination images. However, in the fourth embodiment, the number of display frames 46 is deleted in a case in which the number of display frames 46 is greater than the recognized number of selected examination images. A method of deleting the display frame 46 differs from that in the third embodiment in the process of changing the number of display frames 46 in Step ST4 of the flowchart illustrated in FIG. 9. Since processes other than Step ST4 are the same as those in FIG. 9, the description thereof will not be repeated.

Figure 17:
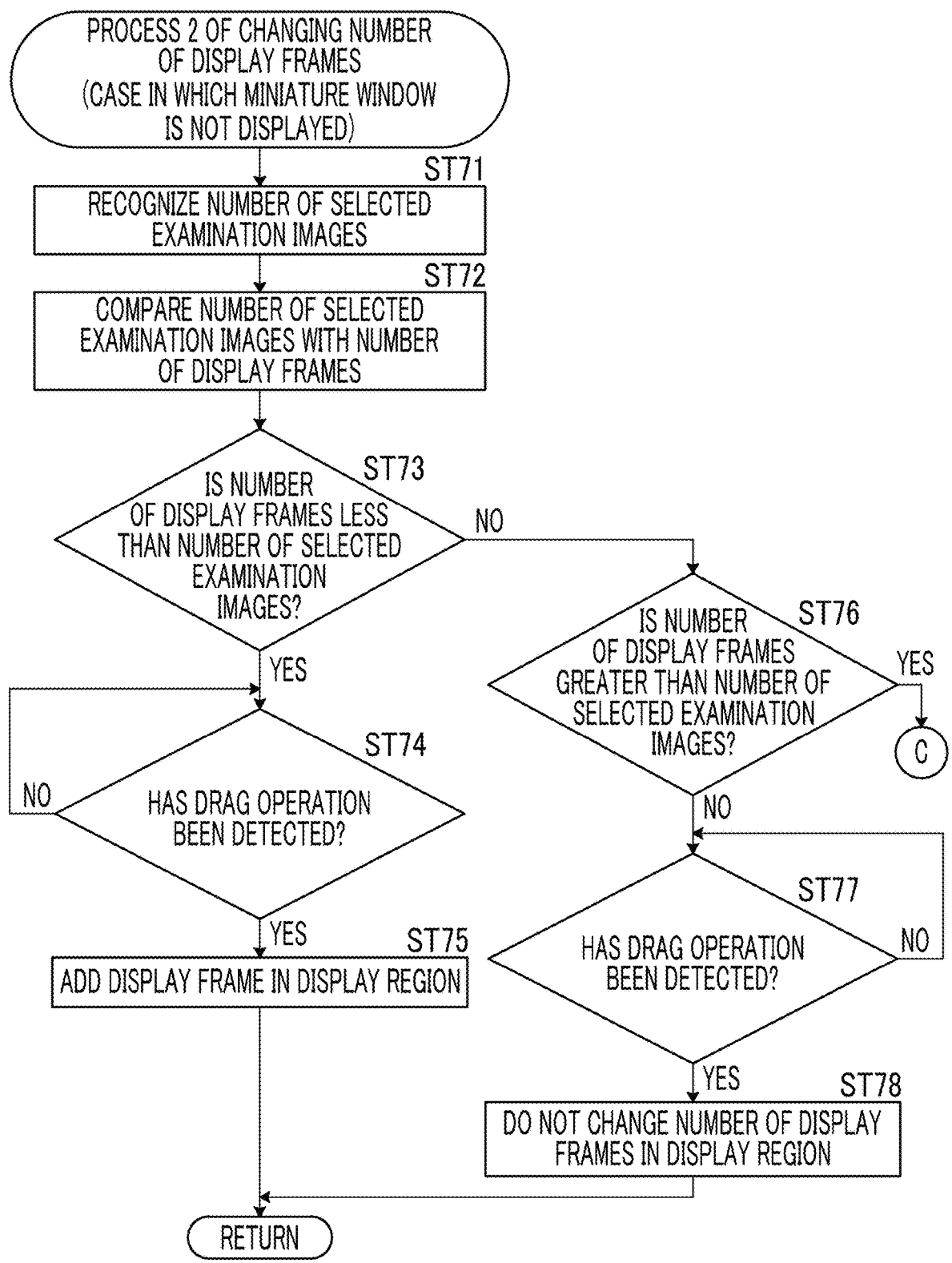
FIG. 17 is another flowchart illustrating a series of processes for changing the number of display frames in a case in which the miniature window is not displayed.

FIG. 17 is a flowchart illustrating a series of processes for changing the number of display frames 46 in a case in which the miniature window 50 is not displayed. In FIG. 17, a process in a case in which the number of display frames 46 is less than the recognized number of selected examination images, that is, a process in Steps ST74 and ST75 is the same as the process in Steps ST44 and ST45 illustrated in FIG. 13. Therefore, the description thereof will not be repeated.

As illustrated in FIG. 17, in a case in which the current number of display frames 46 is equal to or greater than the recognized number of selected examination images (Step ST73; NO) and the current number of display frames 46 is equal to or less than the recognized number of selected examination images (Step ST76; NO), that is, in a case in which the current number of display frames 46 is equal to the recognized number of selected examination images, it is detected whether or not a drag operation of dragging a plurality of thumbnail images selected in the thumbnail image display region 43 from the thumbnail image display region 43 has been performed (Step ST77).

In a case in which the detection result in Step ST77 is "NO" (Step ST77; NO), the process in Step ST77 is repeated until the second display control unit 25 detects a drag operation. In a case in which the detection result in Step ST77 is "YES" (Step ST77; YES), the second display control unit 25 does not change the number of display frames 46 in the image display region 45 since it has been determined in Step ST76 that the current number of display frames 46 is equal to the recognized number of selected examination images (Step ST78).

In contrast, the process proceeds to C in a case in which the determination result in Step ST76 is "YES", that is, in a case in which the current number of display frames 46 is greater than the recognized number of selected examination images (Step ST76; YES).

Figure 18:
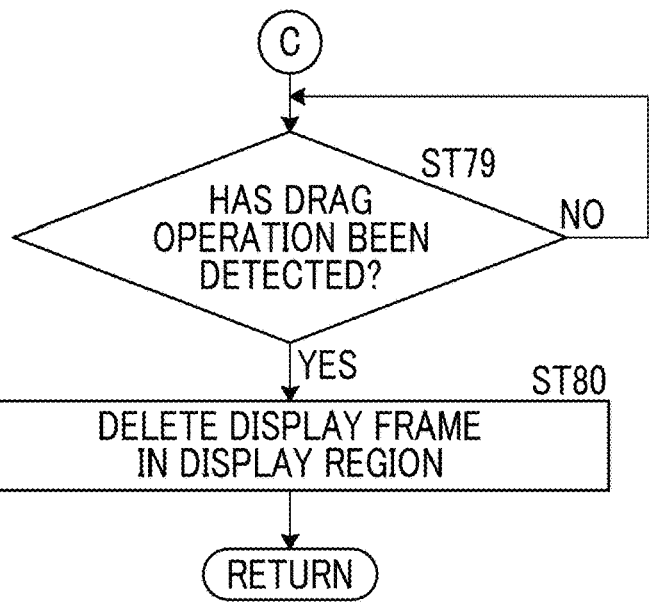
FIG. 18 is a flowchart illustrating a process after C in FIG. 17.

FIG. 18 is a flowchart illustrating a process after C illustrated in FIG. 17. In a case in which the determination result in Step ST76 is "YES", that is, in a case in which the current number of display frames 46 is greater than the recognized number of selected examination images (Step ST76; YES), it is detected whether or not a drag operation of dragging a plurality of thumbnail images selected in the thumbnail image display region 43 from the thumbnail image display region 43 has been performed (Step ST79).

In a case in which the detection result in Step ST79 is "NO" (Step ST79; NO), the process in Step ST79 is repeated until the second display control unit 25 detects a drag operation. In a case in which the detection result in Step ST79 is "YES" (Step ST79; YES), the second display control unit 25 deletes the display frames 46 of the image display region 45 such that the number of display frames 46 in the image display region 45 is equal to the number of selected examination images since it has been determined in Step ST76 that the current number of display frames 46 is greater than the recognized number of selected examination images (Step ST80).

As described above, according to the fourth embodiment, in a case in which a plurality of examination images are laid out in a plurality of display frames 46 arranged in the image display region 45 and the number of display frames 46 is greater than the number of selected examination images, the number of display frames 46 is changed to be equal to the number of examination images. Therefore, it is possible to delete the display frame 46 in which the selected examination image is not disposed. Therefore, one display frame 46 can be set to have a large size in the image display region 45, as compared to a case in which the display frame 46 in which the selected examination image is not disposed is set. As a result, the examination image can be easily interpreted on the display screen 30M.

In the fourth embodiment, the display frames 46 are deleted such that the number of display frames 46 is equal to the number of selected examination images. However, the technology of the present disclosure is not limited thereto. For example, in a case in which the number of selected examination images is an odd number, the number of display frames 46 does not necessarily need to be equal to the number of selected examination images. Specifically, in a case in which the current number of display frames 46 is six and the number of selected examination images is three, two display frames 46 may be deleted such that four display frames 46 are arranged. Therefore, the display frames 46 can be arranged in a 2×2 grid shape on the display screen 30M, which makes it easy to perform comparative interpretation.

Next, a fifth embodiment of the present disclosure will be described. The fifth embodiment is different from the above-described embodiments in that, in a case in which a plurality of selected examination images include the current and past examination images of the same type acquired in the examinations which are the same type and were made on different examination dates, the second display control unit 25 lays out the current examination image and the past examination image at positions adjacent to each other in the column direction or the row direction.

The setting of laying out the current examination image and the past examination image at adjacent positions is performed by, for example, an operation of setting a setting screen. For example, the secondary memory 13 stores an "automatic current examination image and past examination image row direction adjacent display mode" which displays the current examination image and the past examination image so as to be adjacent to each other in the row direction and an "automatic current examination image and past examination image column direction adjacent display mode" which displays the current examination image and the past examination image so as to be adjacent to each other in the column direction.

Figure 19:
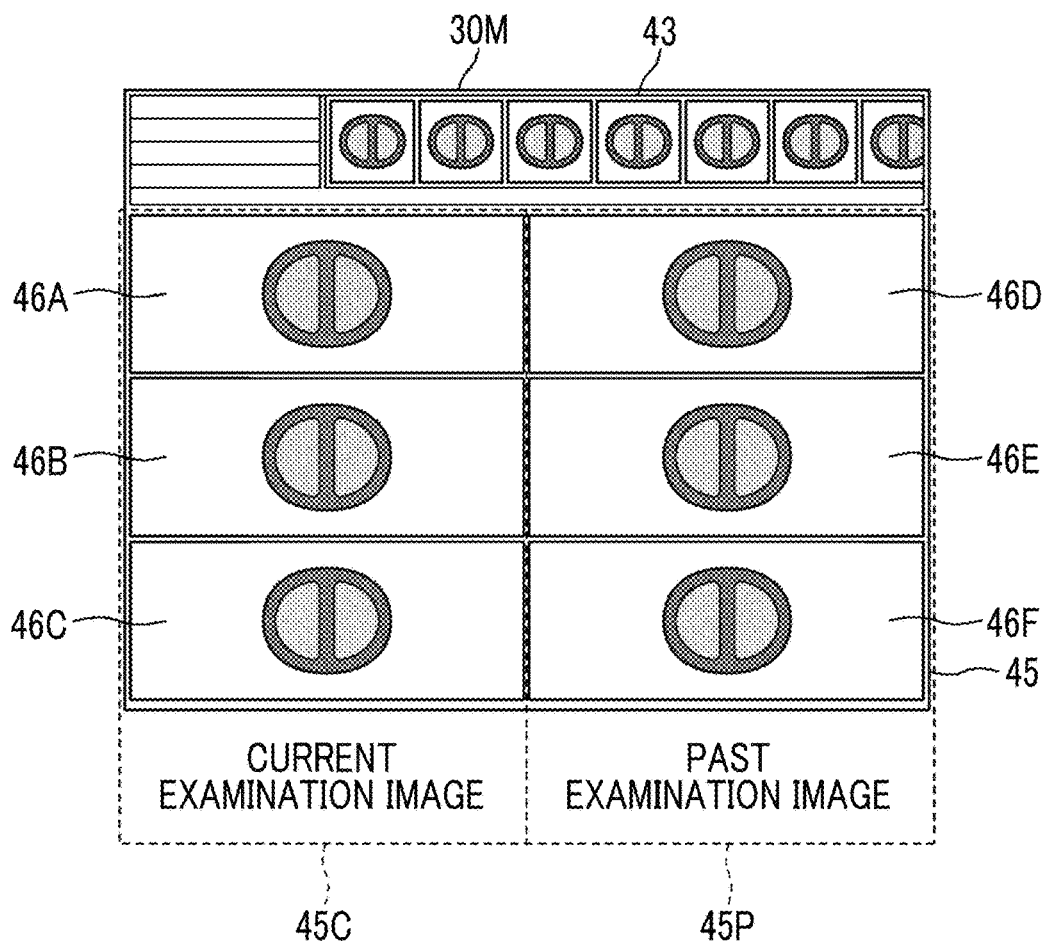
FIG. 19 is a diagram illustrating an example of display for comparative interpretation between a current examination image and a past examination image.

For example, in a case in which the "automatic current examination image and past examination image row direction adjacent display mode" is set on the setting screen, the current examination image and the past examination image among a plurality of selected examination images are displayed so as to be adjacent to each other in the row direction. FIG. 19 is a diagram illustrating an example of display for comparative interpretation of the current examination image and the past examination image.

As illustrated in FIG. 19, in a case in which the display frames 46A to 46F are arranged in a 2×3 grid shape, the second display control unit 25 arranges the display frames 46A to 46C, in which the current examination images are laid out, in a left region 45C of the image display region 45. In addition, the second display control unit 25 arranges the display frames 46D to 46F, in which the past examination images are laid out, in a right region 45P of the image display region 45.

The second display control unit 25 lays out and displays the selected current examination images in the display frames 46A to 46C of the left region 45C. Further, the second display control unit 25 lays out and displays the selected past examination images in the display frames 46D to 46F of the right region 45P.

According to the fifth embodiment, since the current examination image and the past examination image are displayed so as to be adjacent to each other in the row direction, it is easy to perform comparative interpretation for the current examination image and the past examination image and user convenience is improved.

The receiving unit 22 determines the current examination image and the past examination image among a plurality of selected examination images on the basis of accessory information attached to each of the selected examination images, specifically, information such as the type of examination, an examination date, imaging conditions, and an imaging part.

In the fifth embodiment, the current examination images are displayed in the left region 45C of the image display region 45 and the past examination images are displayed in the right region 45P. However, the technology of the present disclosure is not limited thereto. For example, the current examination images may be displayed in the right region 45P of the image display region 45 and the past examination images may be displayed in the left region 45C.

In a case in which the "automatic current examination image and past examination image column direction adjacent display mode" is set on the setting screen, the current examination image is displayed in an upper region of the image display region 45 and the past examination image is displayed in a lower region. In this case, the current examination image may be displayed in the lower region of the image display region 45 and the past examination image may be displayed in the upper region.

The mode set on the setting screen is not limited to the above. For example, the secondary memory 13 may store a "mode that adds a display frame in a case in which the number of display frames is insufficient" and a "mode that does not add a display frame in a case in which the number of display frames is insufficient". In a case in which the "mode that adds a display frame in a case in which the number of display frames is insufficient" is set, the second display control unit 25 performs a process of adding the display frame 46 in the image display region 45 as in the above-described embodiments. In a case in which the "mode that does not add a display frame in a case in which the number of display frames is insufficient" is set, the second display control unit 25 does not perform the process of adding the display frame 46 in the image display region 45.

Therefore, for example, in a case in which the user does not want to add the display frame 46 in the image display region 45, the user sets the mode on the setting screen not to add the display frame 46. As a result, since the user can maintain the desired arrangement configuration of the display frames 46, user convenience is improved.

In the above-described embodiments, one examination image is laid out in each display frame 46 of the image display region 45. However, the one examination image may be a representative image among same-series examination images acquired in the same examination. As described above, the same-series examination images are a plurality of slice images included in a series acquired by, for example, a CT examination. In a case in which the examination image displayed in the display frame 46 is a representative image, a representative image of same-series examination images in the display frame 46 can be selectively displayed, for example, by clicking the examination image currently displayed in the display frame 46.

Further, in the above-described embodiments, each of a plurality of slice images forming the three-dimensional image acquired by the three-dimensional imaging apparatus 2 is the examination image. However, the technology of the present disclosure is not limited thereto. For example, a two-dimensional image acquired by a two-dimensional imaging apparatus, such as a simple X-ray imaging apparatus, may be used as the examination image.

In the above-described embodiments, the viewer region 32 includes the patient information region 41, the examination list region 42, the thumbnail image display region 43, the toolbar region 44, and the image display region 45. However, the technology of the present disclosure is not limited thereto. The viewer region 32 may include at least the thumbnail image display region 43 and the image display region 45.

In the above-described embodiment, the receiving unit 22 receives the selection order in which a plurality of thumbnail images are selected and the second display control unit 25 lays out a plurality of examination images in a plurality of display frames in the selection order. However, the technology of the present disclosure is not limited thereto. For example, for the examination images corresponding to each of the plurality of selected thumbnail images, it is possible to give an order to the examination images on the basis of the accessory information stored in the image storage server 3 together with the examination images. Specifically, in a case in which the examination images are included in same-series examination images in one same examination, the order may be given on the basis of the series number when same-series examination images are acquired.

For the arrangement order in the image display region 45, examples of the selection order of the thumbnail images include an order determined on the basis of any image attribute information in addition to the series number. Specific examples of the image attribute information include a collection date and time and a series description in addition to the series number. The collection date and time means the examination date and the examination time. For example, the arrangement order may be determined in chronological order of the examination date and in chronological order of the examination time or may be determined in reverse chronological order of the examination date and in reverse chronological order of the examination time. The series description means the type of three-dimensional imaging apparatus 2 (for example, a CT apparatus, an MRI apparatus, a PET apparatus, or a SPECT apparatus) used in one series, the imaging conditions (for example, whether or not a contrast agent is used or a radiation dose) during imaging in one series, and an examination part (imaging part) in one series. For example, the arrangement order may be determined from the head to the foot or may be determined from the foot to the head for each examination part. In addition, the order may be determined in a complex manner. First, the arrangement is performed by the series description, for example, a modality name and the arrangement is performed in the order of the collection date in the same modality.

For example, even in a case in which a thumbnail image is randomly selected in the thumbnail image display region 43, the receiving unit 22 may receive the order from the thumbnail image at the left end regardless of the selection order. In this case, the order is not limited to the order from the thumbnail image at the left end. For example, the order may be received from the thumbnail image at the right end to the left. The direction in which the order is given can be set in advance by the user.

In the above-described embodiments, the aspect in which only one display unit 30 is provided has been described. However, the technology of the present disclosure is not limited to the aspect in which one display unit (monitor) 30 is provided and may include a plurality of display units. In the case of a multi-monitor having a plurality of display units 30, for example, the display screen 30M is configured as follows.

A case in which a multi-monitor extended mode in which a plurality of monitors are virtually regarded as one monitor is used is considered. In this case, a monitor region in which one display screen can be displayed is extended. Therefore, in a case in which the display screen is enlarged and displayed, a portion that does not fit on a first monitor which is one monitor is displayed on a second monitor which is another monitor. For example, in a case in which there are eight (=2×4) display frames 46 in the display region of the display screen, four display frames 46 are displayed on the first monitor and the remaining four display frames 46 are displayed on the second monitor.

In this case, the second display control unit 25 can also treat the display screens or the display regions displayed on two monitors of the first monitor and the second monitor as one display screen or one display region. In addition, the second display control unit 25 may treat the display screen or the display region displayed on the first monitor and the display screen or the display region displayed on the second monitor as independent display screens or display regions.

Figure 20:
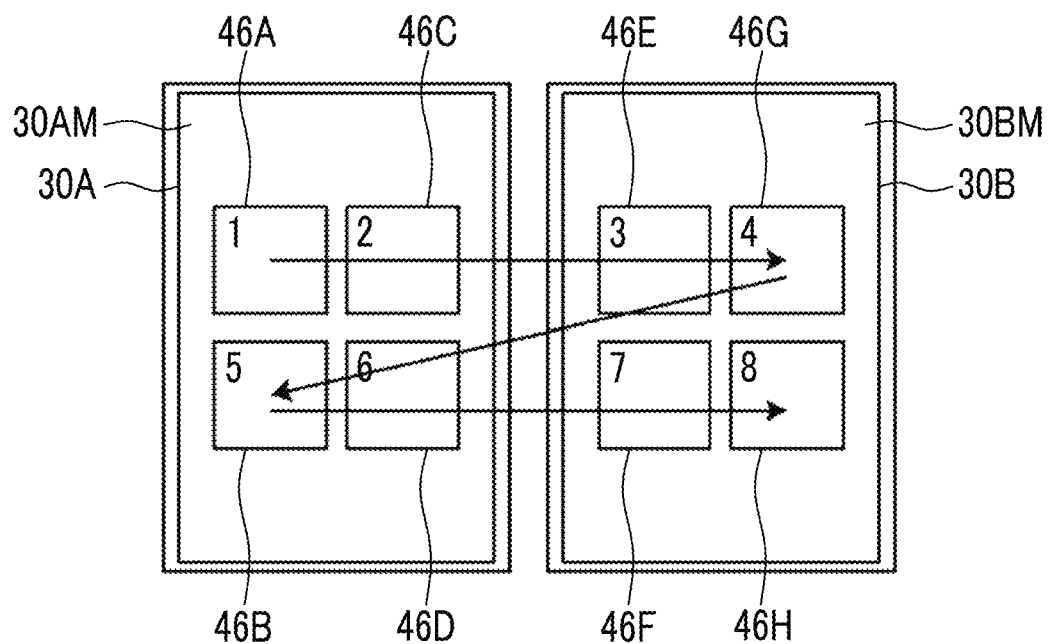
FIG. 20 is a diagram illustrating an example of display screens of two monitors.

In the former case, that is, the treatment of a plurality of display frames in the display region, in which the display screens or the display regions displayed on two monitors of the first monitor and the second monitor are treated as one display screen or one display region, is, for example, as illustrated in FIG. 20. FIG. 20 is a diagram illustrating an example of the display screens of two monitors.

In the example illustrated in FIG. 20, the second display control unit 25 treats a total of four display frames 46A to 46D and a total of four display frames 46E to 46H which are displayed in the upper or lower stages of a first monitor 30A and a second monitor 30B, respectively, as a series of display frames 46A to 46H. The order in which the eight display frames 46A to 46H are used is as follows: the display frames 46A, 46C, 46E, and 46G in the upper stage are prioritized; and, in a case in which the display frames 46A, 46C, 46E, and 46G in the upper stage are filled, the display is shifted to the display frames 46B, 46D, 46F, and 46H in the lower stage.

For example, numbers 1 to 4 are set to the display frames 46A, 46C, 46E, and 46G in the upper stage in order from the left display frame 46A of the first monitor 30A. Numbers 5 to 8 are set to the four display frames 46B, 46D, 46F, and 46H displayed in the lower stage in order from the left display frame 46B of the first monitor 30A. Therefore, in a case in which eight examination images are arranged in the eight display frames 46A to 46H, the examination images are arranged in order from the upper left side of the first monitor 30A to the upper right side of the second monitor 30B as represented by arrows in FIG. 20. In a case in which the four display frames 46A, 46C, 46E, and 46G in the upper stage are filled, the display is moved to the lower stage of the first monitor 30A and the examination images are arranged in order from the lower left side of the first monitor 30A to the lower right side of the second monitor 30B.

Figure 21:
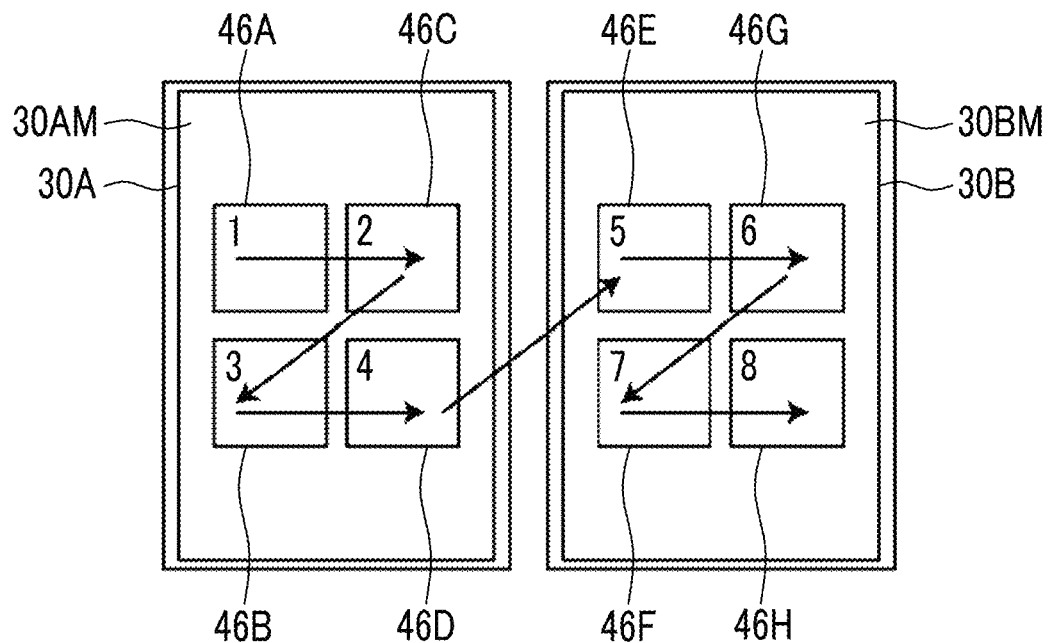
FIG. 21 is a diagram illustrating another example of the display screen of two monitors.

In the latter case, that is, the treatment of a plurality of display frames in the display region, in which the display screen or the display region displayed on the first monitor and the display screen or the display region displayed on the second monitor are treated as independent display screens or display regions, is, for example, as illustrated in FIG. 21. FIG. 21 is a diagram illustrating an example of display screens of two monitors.

In the example illustrated in FIG. 21, unlike FIG. 20, the second display control unit 25 gives priority to four display frames 46A to 46D displayed on the first monitor 30A. In a case in which the four display frames 46A to 46D of the first monitor 30A are filled, the display is shifted to the second monitor 30B.

For example, numbers 1 to 4 are set to the display frames 46A to 46D of the first monitor 30A in order from the upper left display frame 46A to the lower right display frame 46D. Similarly, numbers 1 to 4 are set to the display frames 46E to 46H of the second monitor 30B in order from the upper left display frame 46E to the lower right display frame 46H. Therefore, in a case in which eight examination images are arranged in the eight display frames 46A to 46H, the examination images are arranged in order from the upper left side of the first monitor 30A to the lower right side of the first monitor 30A as represented by arrows in FIG. 21. In a case in which the four display frames 46A to 46D of the first monitor 30A are filled, the display is moved to the upper left side of the second monitor 30B and the examination images are arranged in order from the upper left side of the second monitor 30B to the lower right side of the second monitor 30B.

In the above-described embodiments, for example, the following various processors can be used as the hardware structure of processing units performing various processes, such as the first display control unit 21, the receiving unit 22, the comparison unit 23, the change unit 24, and the second display control unit 25. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:

1. A display control device comprising:
a processor, configured to:
perform first display control to display, on a display screen, a display region in which a plurality of examination images acquired for each examination are displayed and which has a plurality of display frames, each of the plurality of display frames being capable of being laid out as a display position of one of the plurality of examination images, and a selection region which is used to select one or more examination images to be laid out in the plurality of display frames from the plurality of examination images and in which a list of a plurality of thumbnail images obtained by reducing each of the plurality of examination images is displayed;
receive a selection operation of selecting the plurality of thumbnail images from the selection region to select the one or more examination images corresponding to the plurality of thumbnail images;
recognize the number of examination images selected by the selection operation and compares the recognized number of the selected examination images with the current number of display frames;
change the number of display frames in the display region and adds one or more display frame in the display region in a case in which the number of display frames is less than the number of the selected examination images; and
perform second display control to lay out and display the selected examination images in the plurality of display frames,
wherein a command to lay out the examination images in the display frames is an operation of dragging the plurality of thumbnail images selected in the selection region from the selection region to the display region or a miniature window obtained by reducing arrangement of the plurality of display frames and dropping the plurality of thumbnail images to the display region or the miniature window.

2. The display control device according to claim 1, wherein the processor deletes the display frame in a case in which the number of display frames is greater than the number of the selected examination images.

3. The display control device according to claim 1, wherein the processor displays the same number of miniature display frames as the number of the selected examination images in the miniature window in a state in which the plurality of thumbnail images are selected in the selection region and before the same number of display frames as the number of the selected examination images is laid out in the display region.

4. The display control device according to claim 1, wherein, on the display screen, the miniature window is not displayed before the plurality of thumbnail images are selected and is displayed in a case in which the drag of the plurality of selected thumbnail images is started after the plurality of thumbnail images are selected in the selection region.

5. The display control device according to claim 4, wherein the processor displays the miniature window at a position where a drag distance of the thumbnail image from the selection region to the miniature window is shorter than a drag distance of the thumbnail image from the selection region to the display region.

6. The display control device according to claim 1, wherein the processor further receives a selection order in which the plurality of thumbnail images are selected, and
the processor lays out the plurality of examination images in the plurality of display frames in the selection order.

7. The display control device according to claim 1, wherein the processor uses the number and arrangement of the display frames preset for each user as initial display settings for each user at startup.

8. The display control device according to claim 1, wherein the examination images displayed in the display frames in the display region include a representative image of a plurality of examination images of each examination, and
in a case in which the examination image displayed in the display frame is the representative image, the plurality of examination images of each examination are capable of being selectively displayed in the display frame.

9. The display control device according to claim 1, wherein, in a case in which the selected examination images include a current examination image and a past examination image that are the same type and have been acquired in examinations which are the same type and were made on different examination dates, the processor lays out the current examination image and the past examination image at positions adjacent to each other in a column direction or a row direction.

10. A method for operating a display control device, the method comprising:
performing first display control to display, on a display screen, a display region in which a plurality of examination images acquired for each examination are displayed and which has a plurality of display frames, each of the plurality of display frames being capable of being laid out as a display position of one of the plurality of examination images, and a selection region which is used to select one or more examination images to be laid out in the plurality of display frames from the plurality of examination images and in which a list of a plurality of thumbnail images obtained by reducing each of the plurality of examination images is displayed;
receiving a selection operation of selecting the plurality of thumbnail images from the selection region to select the one or more examination images corresponding to the plurality of thumbnail images;

recognizing the number of examination images selected by the selection operation and comparing the recognized number of the selected examination images with the current number of display frames;

changing the number of display frames in the display region and adding one or more display frame in the display region in a case in which the number of display frames is less than the number of the selected examination images; and performing second display control to lay out and display the selected examination images in the plurality of display frames, wherein a command to lay out the examination images in the display frames is an operation of dragging the plurality of thumbnail images selected in the selection region from the selection region to the display region or a miniature window obtained by reducing arrangement of the plurality of display frames and dropping the plurality of thumbnail images to the display region or the miniature window.

11. A non-transitory computer-readable storage medium storing therein a program for operating a display control device, the program causing a computer to:

perform first display control to display, on a display screen, a display region in which a plurality of examination images acquired for each examination are displayed and which has a plurality of display frames, each of the plurality of display frames being capable of being laid out as a display position of one of the plurality of examination images, and a selection region which is used to select the plurality of examination images to be laid out in the plurality of display frames from the plurality of examination images and in which a list of a plurality of thumbnail images obtained by reducing each of the plurality of examination images is displayed;

receive a selection operation of selecting the plurality of thumbnail images from the selection region to select the one or more examination images corresponding to the plurality of thumbnail images;

recognize the number of examination images selected by the selection operation and compares the recognized number of the selected examination images with the current number of display frames;

change the number of display frames in the display region and adds one or more display frame in the display region in a case in which the number of display frames is less than the number of the selected examination images; and perform second display control to lay out and display the selected examination images in the plurality of display frames, wherein a command to lay out the examination images in the display frames is an operation of dragging the plurality of thumbnail images selected in the selection region from the selection region to the display region or a miniature window obtained by reducing arrangement of the plurality of display frames and dropping the plurality of thumbnail images to the display region or the miniature window.

* * * * *